(12) United States Patent
Sato

(10) Patent No.: US 6,310,257 B2
(45) Date of Patent: Oct. 30, 2001

(54) SUBSTITUTED CYCLOPENTENE DERIVATIVES AND METHOD FOR PREPARING THE SAME

(75) Inventor: Fumie Sato, Fujisawa (JP)

(73) Assignees: Nissan Chemical Industries, LTD, Tokyo; Fumie SATO, Kanagawa-ken, both of (JP)

( * ) Notice: Subject to any disclaimer, the term of this patent is extended or adjusted under 35 U.S.C. 154(b) by 0 days.

(21) Appl. No.: 09/774,582

(22) Filed: Feb. 1, 2001

Related U.S. Application Data

(62) Division of application No. 09/666,602, filed on Sep. 20, 2000, which is a division of application No. 09/456,413, filed on Dec. 8, 1999, now Pat. No. 6,191,291, which is a division of application No. 09/149,484, filed on Sep. 8, 1998, now Pat. No. 6,025,518, which is a division of application No. 08/894,879, filed as application No. PCT/JP96/00422 on Feb. 23, 1996, now Pat. No. 5,874,634.

(30) Foreign Application Priority Data

Mar. 2, 1995 (JP) .................................................. 7-68605

(51) Int. Cl.[7] .................................................. C07C 45/58
(52) U.S. Cl. .......................... 568/361; 568/338; 568/366; 549/512; 549/513
(58) Field of Search .................................... 568/338, 361, 568/366; 549/512, 513

(56) References Cited

U.S. PATENT DOCUMENTS 4,367,340    1/1983    Rickard et al. ........................ 549/214
4,703,127    10/1987   Rickard et al. ........................ 549/214

FOREIGN PATENT DOCUMENTS 5539127    5/1980    (JP) .
B1 9891    5/1980    (EP) .

Primary Examiner—Sreeni Padmanabhan

(57) ABSTRACT

A method for making cyclopentene derivatives of the formula (IX):

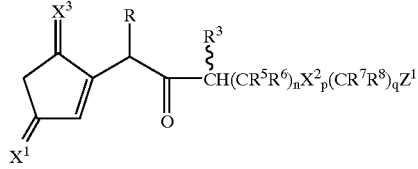

(IX)

by acidolysis of an intermediate epoxide of formula (VIII):

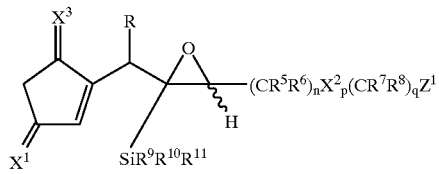

(VIII)

is described.

3 Claims, No Drawings

SUBSTITUTED CYCLOPENTENE DERIVATIVES AND METHOD FOR PREPARING THE SAME

This application is a divisional of co-pending application Ser. No. 09/666,602, filed on Sep. 20, 2000, which is a divisional of application Ser. No. 09/456,413, filed on Dec. 8, 1999, now U.S. Pat. No. 6,191,291 which in turn was a divisional of application Ser. No. 09/149,484, filed on Sep. 8, 1998, now U.S. Pat. No. 6,025,518 which in turn is a divisional of application Ser. No. 08/894,879, filed on Sep. 2, 1997, now U.S. Pat. No. 5,874,634 which in turn is a §371 of PCT/JP96/00422, filed on Feb. 23, 1996, the entire contents of which are hereby incorporated by reference and for which priority is claimed under 35 U.S.C. §120.

TECHNICAL FIELD

This invention relates to substituted cyclopentene derivatives and a method for preparing the same and more particularly, to novel intermediates useful for the production of prostaglandins (to be abbreviated as PG, hereinafter) useful as various drugs, especially $PGE_2$ and 6-keto-$PGE_1$.

BACKGROUND ART

Since PGs exhibit various important physiological actions in minor amounts, active research works have been made thereon for the intended application to drugs. With respect to the extension of PG analogues, it has been attempted in various ways to extend α and ω-chains attached to the five-membered ring moiety. One method capable of free choice of α and ω-chains and efficient introduction is a two-component connecting method. More particularly, direct synthesis is possible by 1,4-addition of a zinc reagent of α-chain to an enone as shown by Scheme 1 (see H. Tsujiyama, N. Ono, S. Okamoto, F. Sato, Tetrahedron Lett., 31, 4481 (1990)).

Scheme 1

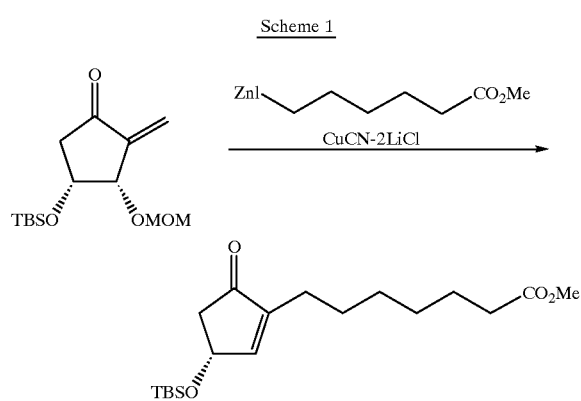

In the synthesis of an intermediate having a double bond in its α-chain, however, it is synthesized by introducing an α-chain into an enone using a vinyl lithium reagent and then effecting functional group conversion as shown by Scheme 2.

Scheme 2

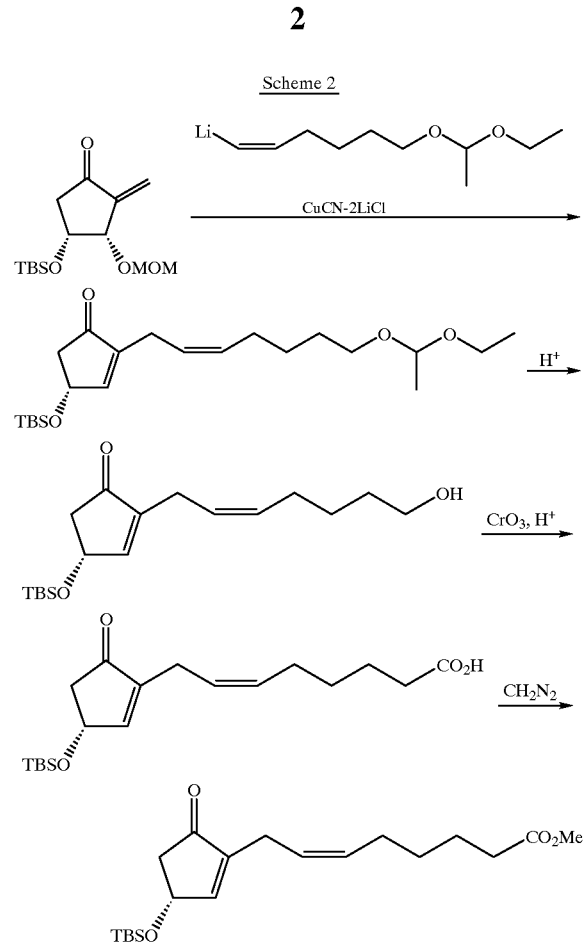

The reason is as follows. It is impossible to form an organic zinc reagent of an α-chain because reaction conditions are severe and the stereo-chemistry of olefin is not maintained. An α-chain is synthesized as an alcohol-protected one because a lithium reagent having an ester group cannot be synthesized. Many stages are thus necessary (see S. Okamoto, Y. Kobayashi, H. Kato, K. Hori, T. Takahashi, J. Tsuji, F. Sato, J. Org. Chem., 53, 5590 (1988)).

Also the route developed by E. J. Corey et al. (Scheme 3) entails much decomposition and hence, low yields since Jones oxidation under severe conditions is utilized. It is industrially inadequate since a heavy metal (Cr) is used (see YAMAMOTO Shozo et al., "Prostaglandins and Related Physiologically Active Compounds", Kodansha, 1981).

Scheme 3

Corey Lactone

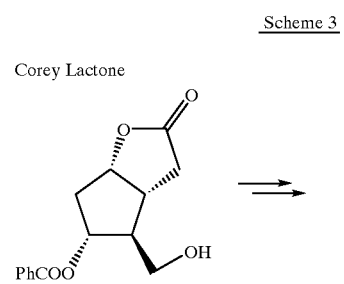

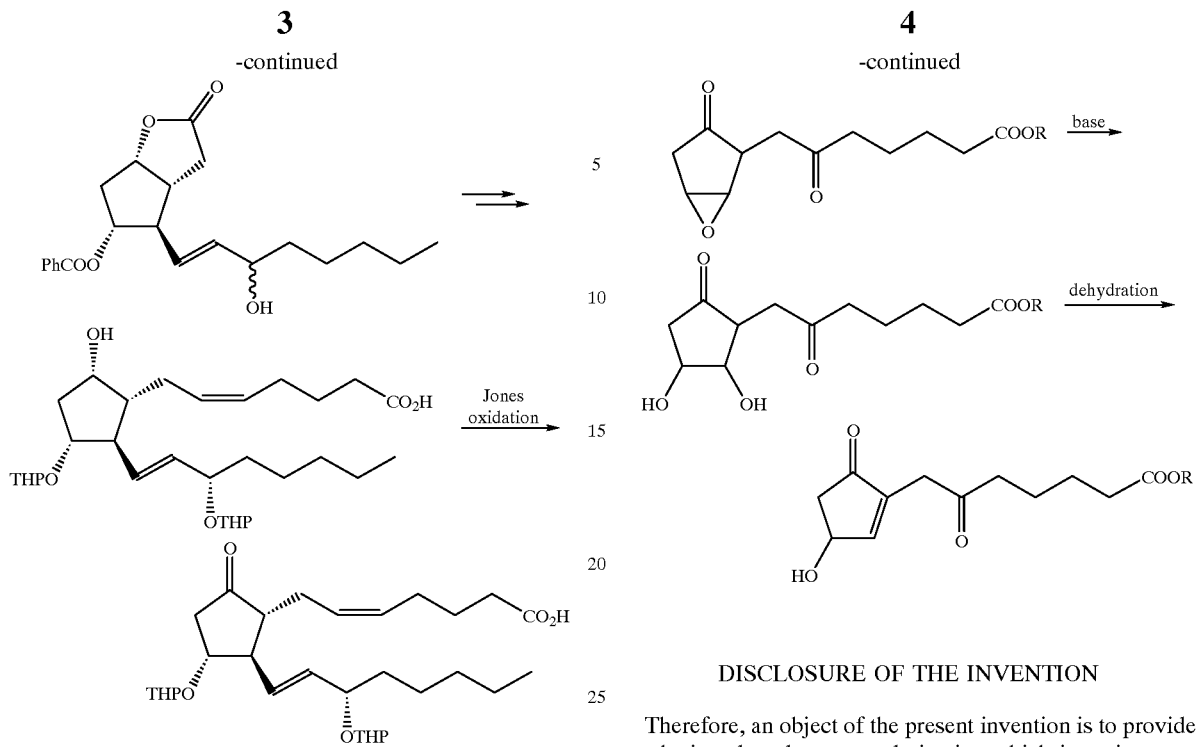

Further, a silyl substituted derivative of formula (VIII) which can be readily synthesized according to the present invention as will be described later is useful in the synthesis of a 6-keto-prostaglandin which now draws attention as a ulcer drug. In the past, an intermediate of this 6-keto-PG has been synthesized through the following route. This technique, however, is not satisfactory as a practical production process since only a racemic modification is obtained and further optical resolution is needed to obtain an optically active substance (see M. Brawner Floyd, Synthetic Communications, 4 (6), 317–323 (1974)).

Scheme 4

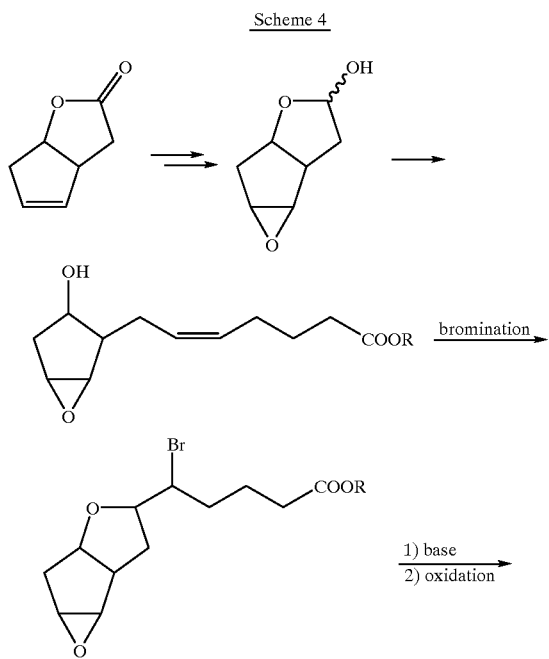

DISCLOSURE OF THE INVENTION

Therefore, an object of the present invention is to provide a substituted cyclopentene derivative which is an intermediate for producing $PGE_2$, 6-keto-$PGE_1$ and analogues in a more advantageous manner and a method for preparing the same.

Making extensive investigations for attaining the above object, the inventor has found that a novel halogenated substituted cyclopentene derivative of formula (I) can be obtained by reacting a compound of formula (II) with a halide of formula (III) or a hydrate thereof in the presence or absence of a Lewis acid as shown below by reaction scheme A; that a novel substituted cyclopentene derivative of formula (V) can be obtained by reacting this novel halogenated substituted cyclopentene derivative of formula (I) with a novel compound of formula (IV) as shown below by reaction scheme B; that a novel epoxy radical-containing substituted cyclopentene derivative of formula (VII) is obtained by oxidizing a compound of formula (VI) embraced in the novel substituted cyclopentene derivative of formula (V) using an oxidizing agent such as peroxides as shown below by reaction scheme C; that a substituted cyclopentene derivative of formula (IX) can be obtained by acidolysis of a compound of formula (VIII) which is a substituted cyclopentene derivative of formula (VII) wherein R is a substituted silyl radical as shown below by reaction scheme D; and that PGs can be advantageously prepared from these substituted cyclopentene derivatives. The present invention is predicated on these findings.

Reaction scheme A

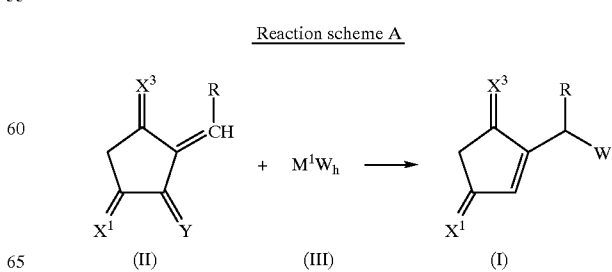

Reaction scheme B

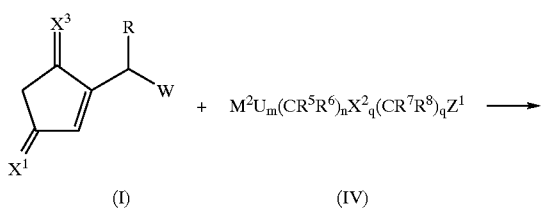

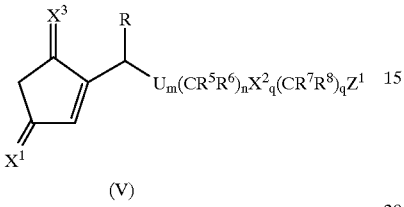

Reaction scheme C

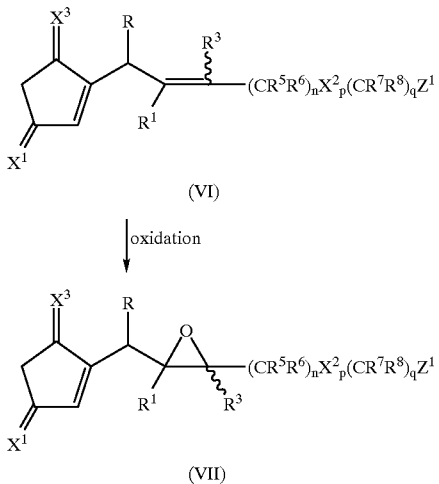

Reaction scheme D

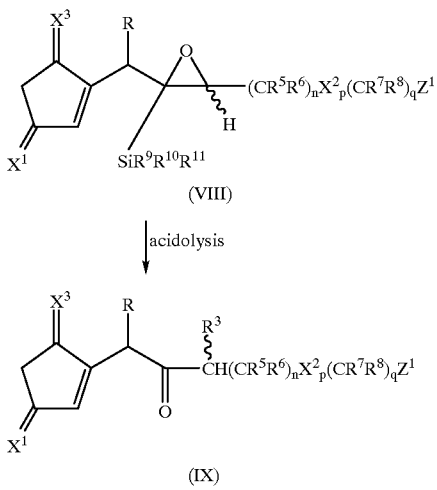

More particularly, among PG synthesis methods, a method represented by "Scheme 5" and known as a two-component method has the advantages of easy reaction control due to the-use of an intermediate having an α-chain and more versatility of ω-chain introduction. The present invention enables synthesis of the following compounds (8b), (10d), etc. in accordance with this method and effective preparation of $PGE_2$ analogues or 6-keto-$PGE_1$ analogues from these compounds as shown by "Scheme 6" and "Scheme 7."

Scheme 5

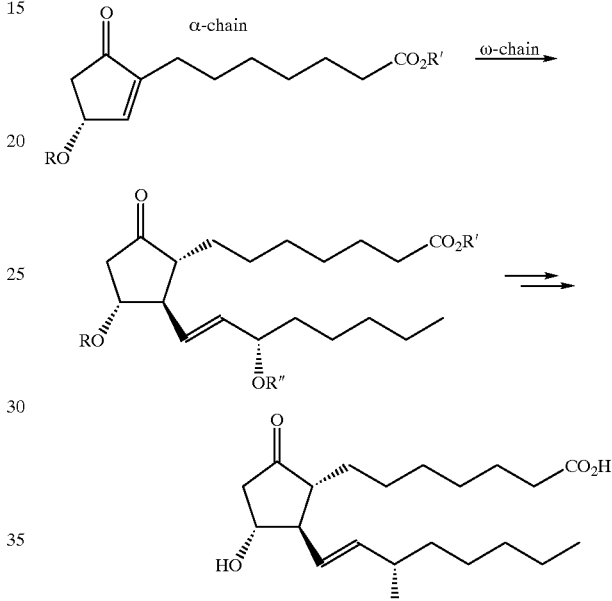

Scheme 6

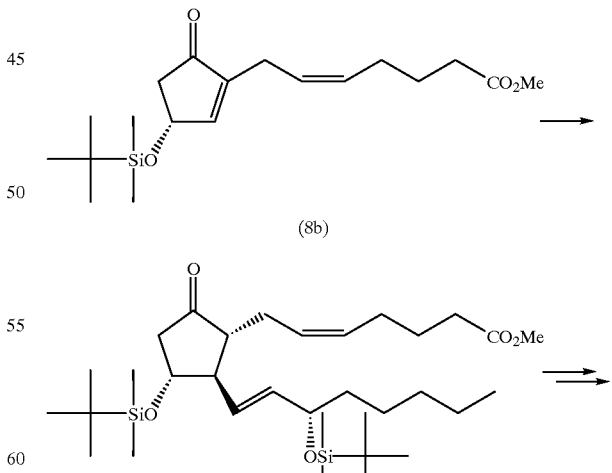

-continued

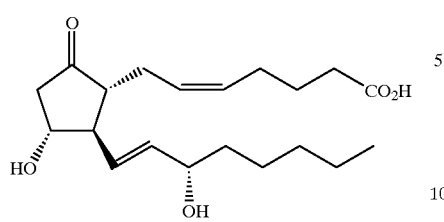

Scheme 7

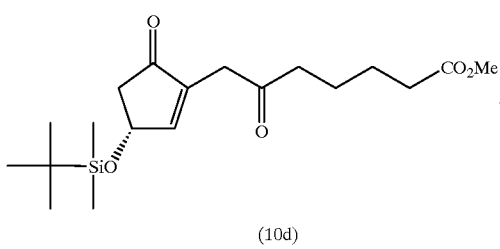
(10d)

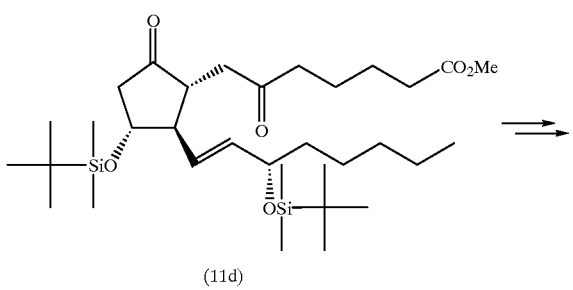
(11d)

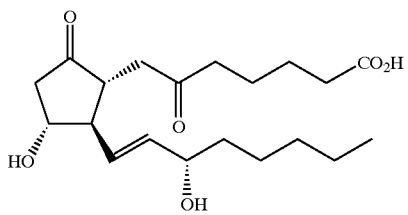

In fact, synthesis of PGs themselves and intermediates (8b), (11d), (13e), (16d), and (10c) is completed as will be shown in Examples and Reference Examples later, with which the invention is acknowledged useful.

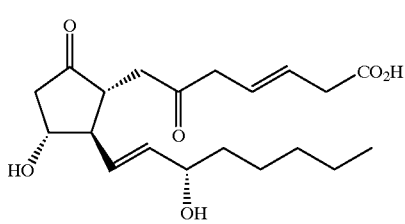
(13e)

-continued

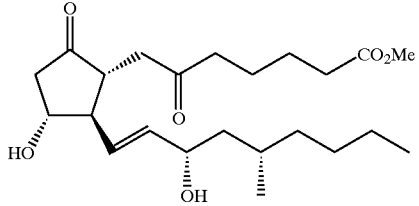
(16d)

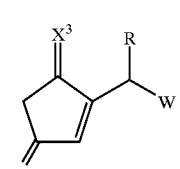
(10c)

Accordingly, the present invention provides (1) to (8) as described below.

(1) A halogenated substituted cyclopentene derivative of the formula (I):

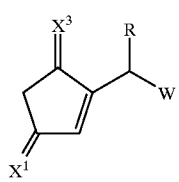
(I)

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms; $X^1$ is ($\alpha$-$OZ^a$, $\beta$-H) or ($\alpha$-H, $\beta$-$OZ^a$), $X^3$ is ($\alpha$-$OZ^d$, $\beta$-H), ($\alpha$-H, $\beta$-$OZ^d$) or oxygen atom, each of $Z^a$ and $Z^d$, which may be the same or different, is a hydrogen atom or a protective radical for a hydroxyl radical; and W is a halogen atom.

(2) A method for preparing a halogenated substituted cyclopentene derivative of the formula (I):

(I)

wherein R, $X^1$, $X^3$, and W are as defined below,
said method comprising the step of reacting a substituted cyclopentane derivative of the formula (II):

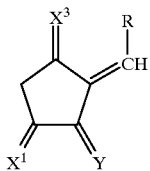

(II)

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms; $X^1$ is ($\alpha$-$OZ^a$, $\beta$-H) or ($\alpha$-H, $OZ^a$), $X^3$ is ($\alpha$-$OZ^d$, $\beta$-H), ($\alpha$-H, $\beta$-$OZ^d$) or oxygen atom, Y is ($\alpha$-$OZ^c$, $\beta$-H) or ($\alpha$-H, $\beta$-$OZ^c$), and each of $Z^a$, $Z^c$ and $Z_d$, which may be the same or different, is a hydrogen atom or a protective radical for a hydroxyl radical, with a halide of the formula (III):

$$M^1W_h \qquad (III)$$

wherein $M^1$ is a metal atom selected from the group consisting of an alkali metal, alkaline earth metal, first transition metal, Al, Zr, and Ce, or quaternary ammonium, w is a halogen atom, and h representative of the valence of said metal or quaternary ammonium is an integer of 1 to 4, or a hydrate thereof in the presence or absence of a Lewis acid.

(3) A method for preparing a substituted cyclopentene derivative of the formula (V):

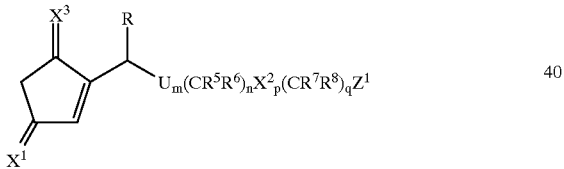

(V)

wherein R, $X^1$, $X^3$, U, $R^5$, $R^6$, $R^7$, $R^8$, $X^2$, m, n, p, q, and $Z^1$ are as defined below, said method characterized by comprising the step of reacting a halogenated substituted cyclopentene derivative of the formula (I):

(I)

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms; X is ($\alpha$-$OZ^a$, $\beta$-H) or ($\alpha$-H, $\beta$-$OZ^a$), $X^3$ is ($\alpha$-$OZ^d$, $\beta$-H), ($\alpha$-H, $\beta$-$OZ^d$) or oxygen atom, each of $Z^a$ and $Z^d$, which may be the same or different, is a hydrogen atom or a protective radical for a hydroxyl radical; and W is a halogen atom with a compound of the formula (IV):

$$M^2U_m(CR^5R^6)_nX^2_p(CR^7R^8)_qZ^1 \qquad (IV)$$

wherein $M^2$ is a substituted borane radical, substituted aluminum radical, substituted zirconium radical or substituted stannyl radical each having a hydrogen atom, alkyl radical having 1 to 9 carbon atoms, cycloalkyl radical having 3 to 12 carbon atoms, aralkyl radical having 7 to 10 carbon atoms, aryl radical having 6 to 8 carbon atoms, alkoxy radical having 1 to 6 carbon atoms, dialkoxy radical having 2 to 12 carbon atoms, alkenyloxy radical having 2 to 6 carbon atoms, substituted phenoxy radical, a cyclopentadienyl radical or halogen atom substituent;

U is a radical selected from the group consisting of $CR^1R^2CR^3R^4$, $CR^1$=$CR^3$, C≡C, and phenylene wherein $R^1$ is a hydrogen atom, alkyl radical having 1 to 9 carbon atoms, alkenyl radical having 2 to 6 carbon atoms, alkynyl radical having 2 to 6 carbon atoms, cycloalkyl radical having 3 to 8 carbon atoms, aralkyl radical having 7 to 10 carbon atoms, aryl radical having 6 to 8 carbon atoms, alkoxy radical having 1 to 6 carbon atoms, alkenyloxy radical having 2 to 6 carbon atoms, halogen atom, substituted silyl radical represented by $SiR^9R^{10}R^{11}$ or substituted stannyl radical represented by $SnR^{14}R^{15}R^{16}$ wherein $R^9$, $R^{10}$ and $R^{11}$ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical, $R^{14}$, $R^{15}$ and $R^{16}$ are independently selected from the group consisting of a hydrogen atom, chlorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical; $R^2$, $R^3$, and $R^4$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; m is an integer of 0 to 6;

$R^5$, $R^6$, $R^7$, and $R^8$ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

$X^2$ is $CR^{12}$=$CR^{13}$, C≡C, phenylene radical, carbonyl radical, oxygen atom or sulfur atom wherein $R^{12}$ and $R^{13}$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; p is an integer of 0 or 1, each of n and q is an integer of 0 to 5; and $Z^1$ is a hydrogen atom, $COOR^y$, CN, OH, $OCOR^z$, $CONR^bR^c$ or $NR^dR^e$ wherein $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^b$ and $R^c$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, in the presence or absence of a metal catalyst.

(4) A compound of the formula (IV):

$$M^2U_m(CR^5R^6)_nX^2_p(CR^7R^8)_qZ^1 \qquad (IV)$$

wherein $M^2$ is a substituted borane radical, substituted aluminum radical, substituted zirconium radical or substituted stannyl radical each having a hydrogen atom, alkyl radical having 1 to 9 carbon atoms, cycloalkyl radical having 3 to 12 carbon atoms, aralkyl radical having 7 to 10 carbon atoms, alyl radical having 6 to 8 carbon atoms, alkoxy radical having 1 to 6 carbon atoms, dialkoxy radical having 2 to 12 carbon atoms, alkenyloxy radical having 2 to 6 carbon atoms, substituted phenoxy radical, a cyclopentadienyl radical or halogen atom substituent;

U is a radical selected from the group consisting of $CR^1R^2CR^3R^4$, $CR^1=CR^3$, $C≡C$, and phenylene wherein $R^1$ is a hydrogen atom, alkyl radical having 1 to 9 carbon atoms, alkenyl radical having 2 to 6 carbon atoms, alkynyl radical having 2 to 6 carbon atoms, cycloalkyl radical having 3 to 8 carbon atoms, aralkyl radical having 7 to 10 carbon atoms, aryl radical having 6 to 8 carbon atoms, alkoxy radical having 1 to 6 carbon atoms, halogen atom, substituted silyl radical represented by $SiR^9R^{10}R^{11}$ or substituted stannyl radical represented by $SnR^{14}R^{15}R^{16}$ wherein $R^9$, $R^{10}$ and $R^{11}$ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical havina 2 to 6 carbon atoms, phenyl radical, tolyl radical, and benzyl radical, $R^{14}$, $R^{15}$ and $R^{16}$ are independently selected from the group consisting of a hydrogen atom, chlorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical; $R^2$, $R^3$, and $R^4$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; m is an integer of 0 to 6;

$R^5$, $R^6$, $R^7$, and $R^8$ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

$X^2$ is $CR^{12}=Cr^{13}$, $C≡C$ phenylene radical, carbonyl radical, oxygen atom or sulfur atom wherein $R^{12}$ and $R^{13}$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; p is an integer of 0 or 1, each of n and q is an integer of 0 to 5; and $Z^1$ is a hydrogen atom, $COOR^y$, ON, OH, $OCOR^z$, $CONR^bR^c$ or $NR^dR^e$ wherein $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^b$ and $R^c$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms.

(5) A compound of the formula (V):

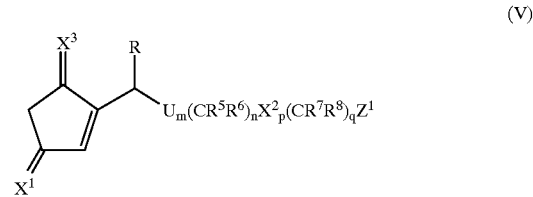

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms;

$X^1$ is ($\alpha$-OZ, $\beta$-H) or ($\alpha$-H, $\beta$-$OZ^a$), $X^3$ is ($\alpha$-$OZ^d$, $\beta$-H), ($\alpha$-H, $\beta$-$OZ^d$) or oxygen atom, each of $Z^a$ and $Z^d$, which may be the same or different, is a hydrogen atom or a protective radical for a hydroxyl radical;

U is a radical selected from the group consisting of $CR^1R^2CR^3R^4$, $CR^1=CR^3$, $C≡C$, and phenylene wherein $R^1$ is a hydrogen atom, alkyl radical having 1 to 9 carbon atoms, alkenyl radical having 2 to 6 carbon atoms, alkynyl radical having 2 to 6 carbon atoms, cycloalkyl radical having 3 to 8 carbon atoms, aralkyl radical having 7 to 10 carbon atoms, aryl radical having 6 to 8 carbon atoms, alkoxy radical having 1 to 6 carbon atoms, alkenyloxy radical having 2 to 6 carbon atoms, halogen atom, substituted silyl radical represented by SiR⁹R¹⁰R¹¹ or substituted stannyl radical represented by SnR¹⁴R¹⁵R¹⁶ wherein R⁹, R¹⁰ and R¹¹ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical, R¹⁴, R¹⁵ and R¹⁶ are independently selected from the group consisting of a hydrogen atom, chlorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical; R², R³, and R⁴ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; m is an integer of 0 to 6;

R⁵, R⁶, R⁷, and R⁸ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

X² is CR¹²=CR¹³, C≡C, phenylene radical, carbonyl radical, oxygen atom or sulfur atom wherein R¹² and R¹³ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; p is an integer of 0 or 1, each of n and q is an integer of 0 to 5; and Z¹ is a hydrogen atom, COORʸ, CN, OH, OCORᶻ, CONRᵇRᶜ or NRᵈRᵉ wherein Rʸ and Rᶻ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, Rᵇ and Rᶜ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, Rᵈ and Rᵉ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms.

(6) A substituted cyclopentene derivative of the formula (VII):

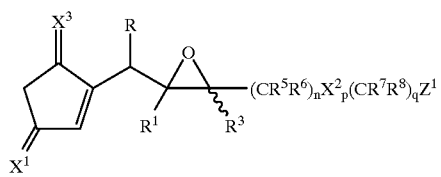

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms;

X¹ is (α-OZᵃ, β-H) or (α-H, β-OZᵃ), X³ is (α-OZᵈ, β-H), (α-H, β-OZᵈ) or oxygen atom, each of Zᵃ and Zᵈ, which may be the same or different, is a hydrogen atom or a protective radical for a hydroxyl radical;

R¹ is a hydrogen atom, alkyl radical having 1 to 9 carbon atoms, alkenyl radical having 2 to 6 carbon atoms, alkynyl radical having 2 to 6 carbon atoms, cycloalkyl radical having 3 to 8 carbon atoms, aralkyl radical having 7 to 10 carbon atoms, aryl radical having 6 to 8 carbon atoms, alkoxy radical having 1 to 6 carbon atoms, alkenyloxy radical having 2 to 6 carbon atoms, halogen atom, substituted silyl radical represented by SiR⁹R¹⁰R¹¹ or substituted stannyl radical represented by SnR¹⁴R¹⁵R¹⁶ wherein R⁹, R¹⁰ and R¹¹ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical, a R¹⁴, R¹⁵ and R¹⁶ are independently selected from the group consisting of a hydrogen atom, chlorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical;

R³ is a hydrogen atom, alkyl radical having 1 to 6 carbon atoms, alkenyl radical having 2 to 6 carbon atoms, alkynyl radical having 2 to 6 carbon atoms or cycloalkyl radical having 3 to 8 carbon atoms;

R⁵, R⁶, R⁷, and R⁸ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

X² is CR¹²=CR¹³, C≡C, phenylene radical, carbonyl radical, oxygen atom or sulfur atom wherein R¹² and R¹³ are independently selected from the group consisting of a hydrogen atom, alkyl radical having 1 to 6 carbon atoms, alkenyl radical having 2 to 6 carbon. atoms, alkynyl radical having 2 to 6 carbon atoms, and cycloalkyl radical having 3 to 8 carbon atoms; p is an integer of 0 or 1, each of n and q is an integer of 0 to 5; and $Z^1$ is a hydrogen atom, $COOR^y$, CN, OH, $OCOR^z$, $CONR^bR^c$ or $NR^dR^e$ wherein $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^b$ and $R^c$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms.

(7) A method for preparing a substituted cyclopentene derivative of the formula (VII):

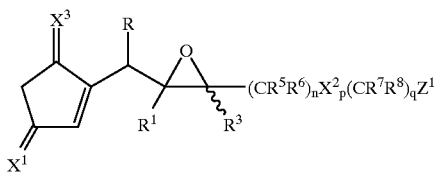

(VII)

wherein R, $X^1$, $X^3$, $X^1$, $R^3$, $R^5$, $R^6$, $R^7$, $R^8$, $X^2$, n, p, q, and $Z^1$ are as defined below, said method characterized by comprising the step of oxidizing with an oxidizing agent such as peroxides a substituted cyclopentene derivative of the formula (VI):

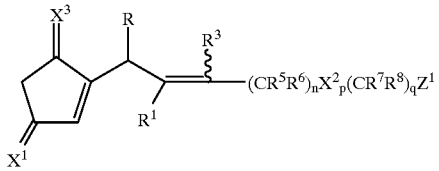

(VI)

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms;

$X^1$ is ($\alpha$-$OZ^a$, $\beta$-H) or ($\alpha$-H, $\beta$-$OZ^a$), $X^3$ is ($\alpha$-$OZ^d$, $\beta$-H), ($\alpha$-H, $\beta$-$OZ^d$) or oxygen atom, each of $Z^a$ and $Z^d$, which may be the same or different, is a hydrogen atom or a protective radical for a hydroxyl radical;

$R^1$ is a hydrogen atom, alkyl radical having 1 to 9 arbon atoms, alkenyl radical having 2 to 6 carbon atoms, lkynyl radical having 2 to 6 carbon atoms, cycloalkyl adical having 3 to 8 carbon atoms, aralkyl radical having 7 to 10 carbon atoms, aryl radical having 6 to 8 carbon atoms, alkoxy radical having 1 to 6 carbon atoms, alkenyloxy radical having 2 to 6 carbon atoms, halogen atom, substituted silyl radical represented by $SiR^9R^{10}R^{11}$ or substituted stannyl radical represented by $SnR^{14}R^{15}R^{16}$ wherein $R^9$, $R^{10}$ and $R^{11}$ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical, $R^{14}$, $R^{15}$ and $R^{16}$ are independently selected from the group consisting of a hydrogen atom, chlorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical;

$R^3$ is a hydrogen atom, alkyl radical having 1 to 6 carbon atoms, alkenyl radical having 2 to 6 carbon atoms, alkynyl radical having 2 to 6 carbon atoms or cycloalkyl radical having 3 to 8 carbon atoms;

$R^5$, $R^6$, $R^7$, and $R^8$ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

$X^2$ is $CR^{12}$=$CR^{13}$, C≡C, phenylene radical, carbonyl radical, oxygen atom or sulfur atom wherein $R^{12}$ and $R^{13}$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; p is an integer of 0 or 1, each of n and q is an integer of 0 to 5; and $Z^1$ is a hydrogen atom, $COOR^y$, CN, OH, $OCOR^z$, $CONR^bR^c$ or $NR^dR^e$ wherein $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, R and R are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms.

(8) A method for preparing a substituted cyclopentene derivative of the formula (IX):

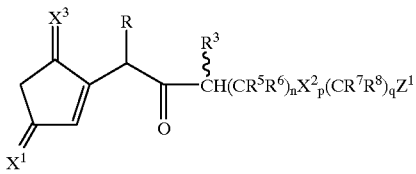

(IX)

wherein R, $X^1$, $X^3$, $R^3$, $R^5$, $R^6$, $R^7$, $R^8$, $X^2$, n, p, q, and $Z^1$ are as defined below, said method characterized by comprising the step of subjecting to acidolysis a substituted cyclopentene derivative of the formula (VIII):

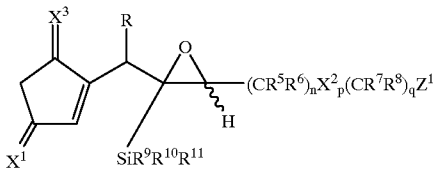

(VIII)

wherein R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms;

$X^1$ is ($\alpha$-$OX^a$, $\beta$-H) of ($\alpha$-H, $\beta$-$OZ^a$), $X^3$ is ($\alpha$-$OZ^d$, $\beta$-H), ($\alpha$-H, $\beta$-$OZ^d$) or oxygen atom, each of $Z^a$ and $Z^b$, which may be the same or different, is a hydrogen atom or a protective radical for a hydroxyl radical;

$R^9$, $R^{10}$ and $R^{11}$ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical;

$R^5$, $R^6$, $R^7$, and $R^8$ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

$X^2$ is $CR^{12}$=$CR^{13}$, C≡C, phenylene radical, carbonyl radical, oxygen atom or sulfur atom wherein $R^{12}$ and $R^{13}$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms; p is an integer of 0 or 1, each of n and a is an integer of 0 to 5; and $Z^1$ is a hydrogen atom, $COOR^y$, CM, OH, $OCOR^z$, $CONR^bR^c$ or $NR^dR^e$ wherein $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^b$ and $R^c$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical saving 2 to 6 carbon atoms, and cycloalkyl radical having 3 to 8 carbon atoms.

BEST MODE FOR CARRYING OUT THE INVENTION

Now the present invention is described in further detail. The invention provides compounds of the following formulae (I), (IV), (V), and (VII).

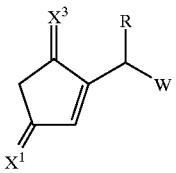

(I)

$$M^2U_m(CR^5R^6)_nX^2_p(CR^7R^8)_qZ^1 \qquad (IV)$$

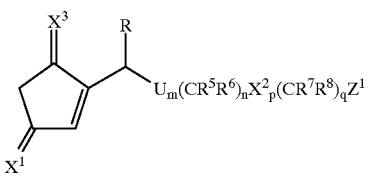

(V)

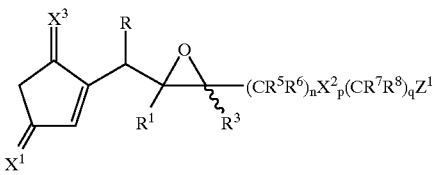

(VII)

In the formulae, R is a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms or alkenylthio radical having 2 to 6 carbon atoms. Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl. The aralkyl radical include benzyl, naphthylmethyl, phenethyl, 1-naphthylethyl and triphenylmethyl which may have a substituent. The aryl radical includes phenyl and substituted phenyl radicals, with exemplary substituents including halogen atoms, trifluoromethyl radicals, alkyl radicals having 1 to 6 carbon atoms (e.g., methyl, ethyl, propyl, isopropyl, butyl, isobutyl, t-butyl, pentyl, and hexyl), alkoxy radicals having 1 to 6 carbon atoms (e.g., methoxy, ethoxy, propoxy, isopropoxy, butoxy, isobutoxy, t-butoxy, cyclopropoxy, ethylenedioxy, 1,2-diphenylethylenedioxy, and propylenedioxy), alkylthio radicals having 1 to 6 carbon atoms (e.g., methylthio, ethylthio, propylthio, isopropylthio, butylthio, isobutylthio, t-butylthio, pentylthio, and hexylthio), alkenyloxy radicals having 2 to 6 carbon atoms (e.g., vinyloxy, propenyloxy, isopropenyloxy, allyloxy, 1-butenyloxy, 2-butenyloxy, 1-pentenyloxy, 2-hexenyloxy, 3-methyl-2-butenyloxy, and 3-methyl-2-pentenyloxy), and alkenylthio radicals having 2 to 6 carbon atoms (e.g., vinylthio, propenylthio, isopropenylthic, allylthio, 1-butenylthio, 2-butenylthio, 1-pentenylthio, 2-hexenylthio, 3-methyl-2-butenylthio, and 3-methyl-2-pentenylthio) as well as a phenyl radical, phenoxy radical, nitro radical, cyano radical, aminu radical and allyl radical. The alkoxy radical includes methoxy, ethoxy, propoxy, isopropoxy, butoxy, isobutoxy, t-butoxy, and cyclopropoxy. The alkylthio radical includes methylthio, ethylthio, propylthio, isopropylthio, butylthio, isobutylthio, t-butylthio, cyclopropylthio, pentylthio, and haxylthio. The alkenylthio radical includes propenylthio, isopropenylthio, allylthio, 1-butenylthio, 2-butenylthio, 1-pentenylthio, 2-hexenylthio, 3-methyl-2-butenylthio, and 3-methyl-2-pentenylthio.

$X^1$ is ($\alpha$-$OZ^a$, $\beta$-H) or ($\alpha$-H, $\beta$-$OZ^a$), $X^3$ is ($\alpha$-$OZ^d$, $\beta$-H) or ($\alpha$-H, $\beta$-$OZ^d$) or oxygen atom, and Y is ($\alpha$-$OZ^c$, $\beta$-H) or ($\alpha$-H, $\beta$-$OZ^c$) wherein each of $Z^a$, $Z^d$ and $Z^c$ is a hydrogen atom or a protective radical for a hydroxyl radical while they may be the same or different. The protective radical may be selected from those radicals commonly used in the PG area, for example, substituted silyl radicals (e.g., trimethylsilyl, triisopropylsilyl, t-butyldimethylsilyl, and t-butyldiphenylsilyl), alkoxyalkyl radicals (e.g., methoxymethyl and ethoxyethyl), aralkyloxyalkyl radicals (e.g., benzyloxymethyl), alkyl radicals (e.g., methyl, ethyl, propyl, isopropyl, and t-butyl), aralkyl radicals (e.g., benzyl and trityl), acyl radicals (e.g., formyl, acetyl and benzoyl), and a tetrahydropyranyl (THP) radical.

W is a halogen atom. The halogen atoms include fluorine, chlorine, bromine, and iodine atoms.

$M^2$ is a substituted borane radical, substituted aluminum radical, substituted zirconium radical or substituted stannyl radical each having a hydrogen atom, alkyl radical having 1 to 9 carbon atoms, cycloalkyl radical having 3 to 12 carbon atoms, aralkyl radical having 7 to 10 carbon atoms, aryl radical having 6 to 8 carbon atoms, alkoxy radical having 1 to 6 carbon atoms, dialkoxy radical having 2 to 12 carbon atoms, alkenyloxy radical having 2 to 6 carbon atoms, substituted phenoxy radical, a cyclopentadienyl radical or halogen atom substituent.

Examples of the alkyl, cycloalkyl, aralkyl, aryl, and alkoxy radicals are those exemplified above. The substituted borane radical includes dithiamylborane, dicyclohexylborane, bicyclo[3.3.1]nona-9-borane, thexylborane, 2-methyl-2,4-pentadiolborane, and catecholborane. The substituted aluminum radical includes diethylaluminum, dimethylaluminum, and diisobutylaluminum. The substituted zirconium radical includes chlorodicyclopentadienylzirconium. The substituted stannyl radical includes trimethylstannyl, triethylstannyl, and tributylstannyl. Preferred are dithiamylborane, dicyclohexylborane, bicyclo[3.3.1]nona-9-borane, and tributylstannyl radicals.

U is $CR^1R^2CR^3R^4$, $CR^1$=$CR^3$, C≡C or phenylene radical.

R is a hydrogen atom, alkyl radical having 1 to 9 carbon atoms, alkenyl radical having 2 to 6 carbon atoms, alkynyl radical having 2 to 6 carbon atoms, cycloalkyl radical having 3 to 8 carbon atoms, aralkyl radical having 7 to 10 carbon atoms, aryl radical having 6 to 8 carbon atoms, alkoxy radical having 1 to 6 carbon atoms, $B^2$ halogen atom, substituted silyl radical represented by $SiR^9R^{10}R^{11}$ or substituted stannyl radical represented by $SnR^{14}R^{15}R^{16}$.

Specifically stated, the alkyl radical includes methyl, ethyl, propyl, isopropyl, butyl, isobutyl, t-butyl, pentyl, hexyl, 1-methylpentyl, heptyl, octyl, 1-methylpentyl, 2-methylpentyl, 1-methylhexyl, 2-methylhexyl, 2,4-dimethylpentyl, 2-ethylpentyl, 2-methylheptyl, 2-ethylhexyl, and 2-propylpentyl.

The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl.

The alkynyl radical includes ethynyl, 1-propynyl, 1-butynyl, and 1-methyl-3-pentynyl.

The cycloalkyl radical includes cyclopropyl, cyclobutyl, cyclopentyl, 4-methylcyclopentyl, cyclohexyl, cyclopropylmethyl, cyclobutylmethyl, and cyclopropylethyl.

The aralkyl radical include benzyl, naphthylmethyl, phenethyl, 1-naphthylethyl and triphenylmethyl which may have a substituent.

The aryl radical includes phenyl and substituted phenyl radicals having a substituent, for example, halogen atoms, trifluoromethyl radicals, alkyl radicals having 1 to 6 carbon atoms (e.g., methyl, ethyl, propyl, isopropyl, butyl, isobutyl, t-butyl, pentyl, and hexyl), alkoxy radicals having 1 to 6 carbon atoms (e.g., methoxy, ethoxy, propoxy, isopropoxy, butoxy, isobutoxy, t-butoxy, cyclopropoxy, ethylenedioxy, 1,2-diphenylethylenedioxy, and propylenedioxy), alkylthio radicals having 1 to 6 carbon atoms (e.g., methylthio, ethylthio, propylthio, isopropylthio, butylthio, isobutylthio, t-butylthio, pentylthio, and hexylthio), and the aforementioned alkenylthio radicals as well as a phenyl radical, phenoxy radical, nitro radical, cyano radical, amino radical and allyl radical.

The alkoxy radical includes methoxy, ethoxy, propoxy, isopropoxy, butoxy, isobutoxy, t-butoxy, and cyclopropoxy.

The halogen atom includes fluorine, chlorine, bromine, and iodine atoms.

$R^9$, $R^{10}$ and $R^{11}$ in the substituted silyl radical $SiR^9R^{10}R^{11}$ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkenyloxy radical having 2 to 6 carbon atoms, and alkoxy radical having 1 to 6 carbon atoms. Specifically stated, the alkyl radical includes methyl, ethyl, propyl, isopropyl, butyl, isobutyl, t-butyl, pentyl, hexyl, 1-methylpentyl, 2-methylpentyl, and tetrahydropyranyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical include cyclopropyl, cyclobutyl, cyclopentyl, 4-methylcyclopentyl, cyclohexyl, cyclopropylmethyl, cyclobutylmethyl, and cyclopropylethyl. The alkoxy radical includes methoxy, ethoxy, propoxy, isopropoxy, butoxy, and t-butoxy. The alkenyloxy radical includes vinyloxy, propenyloxy, isocropenyloxy, allyloxy, 1-butenyloxy, 2-butenyloxy, 1-pentenyloxy, 2-hexenyloxy, 3-methyl-2-butenyloxy, and 3-methyl-2-pentenyloxy.

Examples of the substituted silyl radical include trimethylsilyl, triethylsilyl, triisopropylsilyl, t-butyldimethylsilyl, dimethylisopropylsilyl, diethylisopropylsilyl, triphenylsilyl, tribenzylsilyl, t-butyldiphenylsilyl, trichlorosilyl, methyldichlorosilyl, dimethylchlorosilyl, dichloromethylsilyl, trifluorosilyl, methyldifluorosilyl, dimethylfluorosilyl, triethoxysilyl, ethyldimethoxysilyl, ethyldiethoxysilyl, ethyldiisopropoxysilyl, diethylethoxysilyl, dimethylmethoxysilyl, dimethylethoxysilyl, diethoxymethylsilyl, dimethylisopropoxysilyl, and methyldiethoxysilyl. The preferred radical is trimethylsilyl.

$R^{14}$, $R^{15}$ and $R^{16}$ in the substituted stannyl radical $SnR^{14}R^{15}R^{16}$ are independently selected from the group consisting of a hydrogen atom, chlorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, and alkoxy radical having 1 to 6 carbon atoms. Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical include cyclopropyl, cyclobutyl, cyclopentyl, 4-methylcyclopentyl, cyclohexyl, cyclopropylmethyl, cyclobutylmethyl, and cyclopropylethyl. The alkoxy radical includes methoxy, ethoxy, propoxy, isopropoxy, butoxy, and t-butoxy. The alkenyloxy radical includes vinyloxy, propenyloxy, isopropenyloxy, allyloxy, 1-butenyloxy, 2-butenyloxy, 1-pentenyloxy, 2-hexenyloxy, 3-methyl-2-butenyloxy, and 3-methyl-2-pentenyloxy.

Examples of the substituted stannyl radical include trimethylstannyl, tributylstannyl, and dibutylvinylstannyl. The preferred radical is tributylstannyl.

$R^2$, $R^3$, and $R^4$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms. Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl.

Letter m is an integer of 0 to 6.

$R^5$, $R^6$, $R^7$, and $R^8$ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical. Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl. The alkoxycarbonyl radical includes methoxycarbonyl, ethoxycarbonyl, propoxycarbonyl, isopropoxycarbonyl, butoxycarbonyl and t-butoxycarbonyl. The alkenyloxycarbonyl radical includes vinyloxy, propenyloxy, isopropenyloxy, allyloxy, 1-butenyloxy, 2-butenyloxy, I-pentenyloxy, 2-hexenyloxy, 3-methyl-2-butenyloxy, and 3-methyl-2-pentenyloxy.

$X^2$ is $CR^{12}=CR^{13}$, $C\equiv C$, phenylene radical, carbonyl radical, oxygen atom or sulfur atom wherein $R^{12}$ and $R^{13}$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms.

Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl.

The phenylene radical is selected from the group consisting of 1,2-, 1,3- and 1,4-phenylene radicals which may be substituted with substituents, for example, halogen atoms, trifluoromethyl, alkyl radicals having 1 to 6 carbon atoms (e.g., methyl, ethyl, propyl, isopropyl, butyl, isobutyl, t-butyl, pentyl, hexyl, 1-methylpentyl, and 2-methylpentyl), alkoxy radicals having 1 to 6 carbon atoms (e.g., methoxy, ethoxy, propoxy, isopropoxy, butoxy, isobutoxy, and t-butoxy, and cyclopropoxy), alkylthio radicals having 1 to 6 carbon atoms (e.g., methylthio, ethylthio, propylthio, isopropylthio, butylthio, isobutylthio, t-butylthio, pentylthio, and hexylthio), alkenylthio radicals as mentioned above, phenyl, phenoxy, nitro, cyano, amino, and aryl radicals.

Letter p is an integer of 0 or 1 and each of n and q is an integer of 0 to 5.

$Z^1$ is a hydrogen atom, $COOR^y$, CN, OH, $OCOR^z$, $CONR^bR^c$ or $NR^dR^e$. $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms. Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl.

$R^b$ and $R^c$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms. Specifically stated, the alkyl radical includes methyl, ethyl, propyl, isopropyl, butyl, isobutyl, t-butyl, pentyl, hexyl, 1-methylpentyl, and 2-methylpentyl The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl. The alkoxy radical includes methoxy, ethoxy, propoxy, isopropoxy, butoxy, and t-butoxy.

$R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms. Specifically stated, the alkyl radical includes methyl, ethyl, propyl, isopropyl, butyl, isobutyl, t-butyl, pentyl, hexyl, 1-methylpentyl, and 2-methylpentyl. The alkenyl radical includes vinyl, propenyl, isopropenyl, allyl, 1-butenyl, 2-butenyl, 1-pentenyl, 2-hexenyl, 3-methyl-2-butenyl, and 3-methyl-2-pentenyl. The alkynyl radical includes ethynyl, 1-propynyl, 1-butynyl, and 1-methyl-3-pentynyl. The cycloalkyl radical includes cyclopropyl, cyclobutyl, cyclopentyl, 4-methylcyclopentyl, cyclohexyl, cyclopropylmethyl, cyclobutylmethyl, and cyclopropylethyl.

In another aspect, the present invention provides preparation methods according to the following reaction schemes A to D.

Reaction scheme A

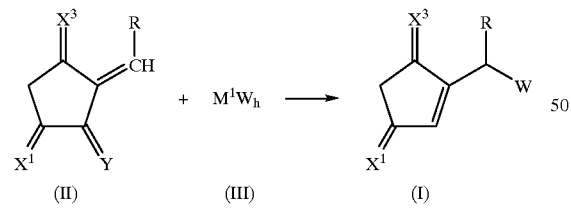

Reaction scheme B

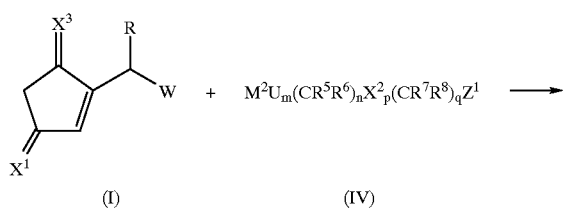

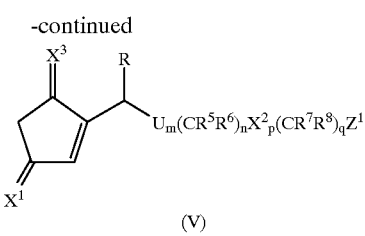

Reaction scheme C

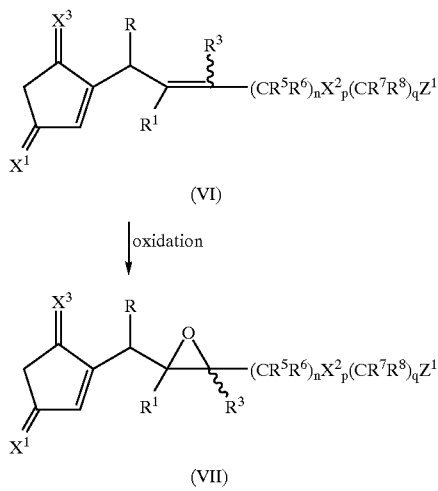

Reaction scheme D

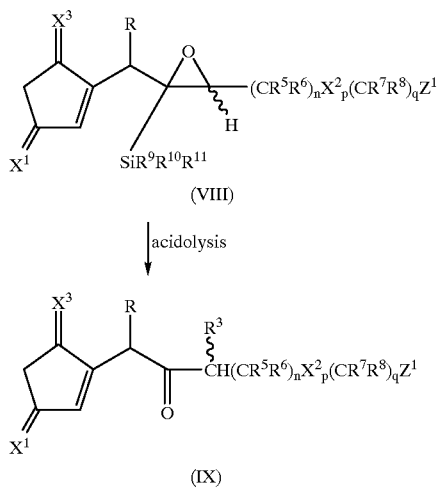

In the formulae, $M^1$ is a metal atom selected from the group consisting of alkali metals, alkaline earth metals, first transition metals, Al, Zr, and Ce, or quaternary ammonium. Examples include lithium, sodium, potassium, magnesium, calcium, titanium, zirconium, cerium, nickel, zinc, aluminum, tetrabutylammonium, tetraethylammonium, benzyltrimethylammonium, benzyltriethylammonium, trioctylmethylammonium. h which is representative of the valence of the above-mentioned metal or quaternary ammonium is an integer of 1 to 4. It is understood that the remaining radicals are as previously defined.

In the above-mentioned reaction scheme A, the substituted cyclopentane derivatives of formula (II) used as a starting material in the present invention are known compounds when $X^3$ is an oxygen atom, which can be synthesized by the method of JP-A 128/1990 or EP 0295880(A1) or the like. Those substituted cyclopentane derivatives of formula (II) wherein $X^3$ is ($\alpha$-$OZ^d$, $\beta$-H) or ($\alpha$-H, $\beta$-$OZ^d$) can be synthesized by reacting a substituted cyclopentene derivative wherein $X^3$ is an oxygen atom with a reducing agent and optionally introducing a protective radical.

With regard to the reaction of a substituted cyclopentane derivative of formula (II) wherein $X^3$ is an oxygen atom with a reducing agent, 0.5 to 10 equivalents, especially 0.8 to 5 equivalents of the reducing agent is preferably used relative to the substituted cyclopentane derivative. Exemplary reducing agents include sodium boron hydride, sodium boron hydride-cerium trichloride mixtures, aluminum isobutyl hydride, aluminum lithium hydride, aluminum hydride, trialkoxyaluminum lithium hydride (the alkoxy moieties may be the same or different and include, for example, methoxy, ethoxy, propoxy, isopropoxy, butoxy, t-butoxy, ethylenedioxy, 1,2-diphenylethylenedioxy, and propylenedioxy), zinc boron hydride, K-selectride, L-selectride, Red-Al, and triethylsilane. There may be used any of reaction solvents which do not inhibit reaction, for example, methanol, ethanol, isopropanol, benzene, hexane, methylene chloride, tetrahydrofuran (THF), toluene, 1,4-dioxane, diethyl ether, and dimethoxyethane (DME) alone or in admixture. The reaction temperature ranges from −100° C. to the reflux temperature of the solvent, usually from −80° C. to 50° C. The reaction time is usually from 5 minutes to 50 hours although it varies with the substrate, solvent and reaction temperature.

With regard to the reaction of a substituted cyclopentane derivative of formula (II) with a halide of formula (III), 1 to 5 equivalents, especially 1.5 to 3 equivalents of the halide of formula (III) is preferably used relative to the substituted cyclopentane derivative of formula (II). Preferred examples of the halide of formula (III) to be combined include sodium bromide, potassium bromide, sodium iodide, potassium iodide, and tetrabutylammonium bromide. In reaction scheme A, reaction of the compound of formula (II) with the compound of formula (III) may be carried out in the presence or absence of a Lewis acid. Examples of the Lewis acid include boron trifluoride-diethyl ether complexes, trialkoxyaluminum, tetraalkoxytitanium, tetrahalotitanium, monoalkoxytrihalotitanium, dialkoxydihalotitanium, trialkoxyhalotitanium (the halo moieties, which may be the same or different, include fluorine, chlorine, bromine and iodine, and the alkoxy radicals, which may be the same or different, include methoxy, ethoxy, propoxy, isopropoxy, butoxy, t-butoxy, ethylenedioxy, 1,2-diphenylethylenedioxy, and propylenedioxy). The Lewis acid, if present, is used in an amount of 0.5 to 5 equivalents relative to the substituted cyclopentane derivative of formula (II). It is especially preferred to use 1 to 2 equivalents of boron trifluoride-diethyl ether complex or tetraisopropoxytitanium. There may be used any of reaction solvents which do not inhibit reaction, for example, acetone, benzene, hexane, methylene chloride, tetrahydrofuran (THF), toluene, 1,4-dioxane, diethyl ether, and dimethoxyethane (DME) alone or in admixture, with acetone being preferred. The reaction temperature ranges from −100° C. to the reflux temperature of the solvent, usually from −20° C. to 50° C. The reaction time is usually from 5 minutes to 50 hours although it varies with the substrate, solvent and reaction temperature.

The halogenated cyclopentene derivatives of formula (I) which are synthesized from a substituted cyclopentane derivative of formula (II) and a halide of formula (III) in this way are novel compounds.

With regard to the synthesis of organometallic reagents of formula (IV), those reagents wherein $R^3$ in $CR^1R^2CR^3R^4$ or $CR^1$=$CR^3$ is a hydrogen atom and $M^2$ is a substituted borane radical can be synthesized by adding corresponding boron hydrides to those reagents wherein U is $CR^1$≡C. The alkenyl boron compounds in cis form of formula (IV) can be synthesized in accordance with the reports of Negishi and Suzuki (E. Negishi et al., J. Organomet. Chem., 92, C4 (1975), A. Suzuki et al., Chem. Rev., 1995, 95, 2457).

In reaction scheme B, the reaction of a substituted cyclopentene derivative of formula (I) with an organo-metallic reagent of formula (IV) preferably uses 1 to 10 equivalents, especially 1.5 to 5 equivalents of the organometallic reagent of formula (IV) relative to the substituted cyclopentene derivative of formula (I). The metal catalyst, if used, is preferably added in an amount of 0.001 to 1 equivalent, especially 0.01 to 0.1 equivalent relative to the substituted cyclopentene derivative of formula (I). Examples of the metal catalyst include $Pd(PPh_3)_4$, $Pd_2(dba)_3$—$CHCl_3$ wherein dba is dibenzalacetone, $Pd(OCOMe)_2$, $PdCl_2$, $PdCl_2(PPh_3)_2$, $PdCl_2(dppf)$ wherein dppf is 1,1'-bisdiphenylphosphinoferrocene, $Na_2PdCl_4$, $PdCl_2(MeCN)_2$, $Ni(PPh_3)_4$, $Ni(COD)_2$ wherein COD is cyclooctadiene, and $NiCl_2$. If necessary, a phosphine ligand is preferably used in an amount of 0.001 to 1 equivalent, especially 0.01 to 1 equivalent relative to the substituted cyclopentene derivative of formula (I). Examples of the phosphine ligand include triphenylphosphine, 1,3-bisdiphenylphosphinopropane, 1,2-bisdiphenylphosphinobutane, 2,2'-bisdiphenylphosphino-1, 1'-binaphthyl, and 1,1'-bisdiphenylphosphinoferrocene. There may be used any of reaction solvents which do not inhibit reaction, for example, acetone, benzene, hexane, methylene chloride, 1,2-dichloroethane, THF, toluene, 1,4-dioxane, diethyl ether, and DME alone or in admixture, with benzene and THF being preferred. Reaction proceeds under neutral to basic conditions, preferably under basic conditions. For the basic catalyst, organic amines such as triethylamine, pyridine, N-methylmorpholine, and diazabicycloundecene or inorganic bases such as sodium hydroxide, potassium hydroxide, sodium carbonate, potassium carbonate, sodium hydrogen carbonate, and potassium hydrogen phosphate may be used alone or in admixture and if desired, in an aqueous solution form. While the amount of basic catalyst used varies with a particular base, the basic catalyst can be used in an amount of 0.001 to 100 equivalents or as a solvent, preferably in an amount of 0.01 to 50 equivalents relative to the compound of formula (I). The reaction temperature ranges from −100° C. to the reflux temperature of the solvent, usually from −20° C. to 100° C. The reaction time is usually from 5 minutes to 50 hours although it varies with the substrate, solvent and reaction temperature.

Especially when $M^2$ is a substituted borane or substituted stannyl radical, the metal catalyst is preferably selected from $Pd(PPh_3)_4$, $Pd_2(dba)_3$—$CHCl_3$, $Pd(OCOMe)_2$, $PdCl_2$, $PdCl_2(PPh_3,)$, and $PdCl_2(dppf)$.

The halogenated cyclopentene derivatives of formula (V) which are synthesized from a substituted cyclopentene derivative of formula (I) and an organometallic reagent of formula (IV) in this viay are novel compounds.

Reaction scheme C involves the reaction of a substituted cyclopentene derivative of formula (VI) with an oxidizing agent. Examples of the oxidizing agent include peracids (e.g., meta-chloroperbenzoic acid, perbenzoic acid, trifluoroperacetic acid, and peracetic acid) and combinations of a peroxide and a metal (exemplary peroxides are hydrogen peroxide, t-butylhydroperoxide, 1,2,3,4-tetrahydronaphthalene-1-hydroperoxide, and exemplary metals are vanadium, titanium, molybdenum, and tungsten in salt form). Preferably 1 to 10 equivalents of the oxidizing agent is used relative to the substituted cyclopentene derivative of formula (I), especially 1 to 5 equivalents of the peracid is used where R in formula (VI) is a substituted silyl radical. There may be used any of reaction solvents which do not inhibit reaction, for example, acetone, benzene, hexane, methylene chloride, 1,2-dichloroethane, THF, toluene, 1,4-dioxane, diethyl ether, DME, and chloroform alone or in admixture, with methylene chloride and chloroform being preferred. The reaction temperature ranges from −100° C. to the reflux temperature of tne solvent, usually from −20° C. to 70° C. The reaction time is usually from 5 minutes to 50 hours although it varies with the substrate, solvent and reaction temperature.

The substituted cyclopentene derivatives of formula (VII) which are synthesized from a substituted cyclopentene derivative of formula (VI) and an oxidizing agent are novel compounds.

Reaction scheme D involves the reaction of a substituted cyclocentene derivative of formula (VII) with an acid. Examples of the acid include Lewis acids such as boron trifluoride-diethyl ether complexes, trialkoxyaluminum, tetraalkoxytitanium, tetrahalotitanium, monoalkoxytrihalotitanlum, dialkoxydihalotitanium, trialkoxyhalotitanium (the halo moieties, which may be the same or different, include fluorine, chlorine, bromine and iodine, and the alkoxy radicals, which may be the same or different, include methoxy, ethoxy, propoxy, isopropoxy, butoxy, t-butoxy, ethylenedioxy, 1,2-diphenylethylenedioxy, and propylenedioxy); mineral acids such as hydrochloric acid and sulfuric acid; and organic acids such as acetic acid, para-toluenesulfonic acid, and methanesulfonic acid. Preferably 0.1 to 10 equivalents of the acid is used relative to the substituted cyclopentene derivative of formula (VII). It is especially preferred to use 0.5 to 3 equivalents of boron trifluoride-diethyl ether complex or tetraisopropoxytitanium. There may be used any of reaction solvents which do not inhibit reaction, for example, methanol, ethanol, isopropanol, acetone, benzene, hexane, methylene chloride, 1,2-dichloroethane, THF, toluene, 1,4-dioxane, diethyl ether, DME, and chloroform alone or in admixture, with methanol, ethanol, and isopropanol being preferred. The reaction temperature ranges from −100° C. to the reflux temperature of the solvent, usually from −20° C. to 70° C. The reaction time is usually from 5 minutes to 50 hours although it varies with the substrate, solvent and reaction temperature.

The present invention ensures easy synthesis of intermediate substituted cyclopentene derivatives useful for the synthesis of PG's and facilitates commercially advantageous production of PG's from the resulting substituted cyclopentene derivatives.

Examples and Reference Examples are given below by way of illustration of the invention although the invention is not limited to these Examples and Reference Examples. In the following Examples, Me is methyl, Et is ethyl, Ph is phenyl, MOM is methoxymethyl, dppf is 1,1'-bisdiphenylphosphinoferrocene, and dba is dibenzalacetone.

EXAMPLE 1

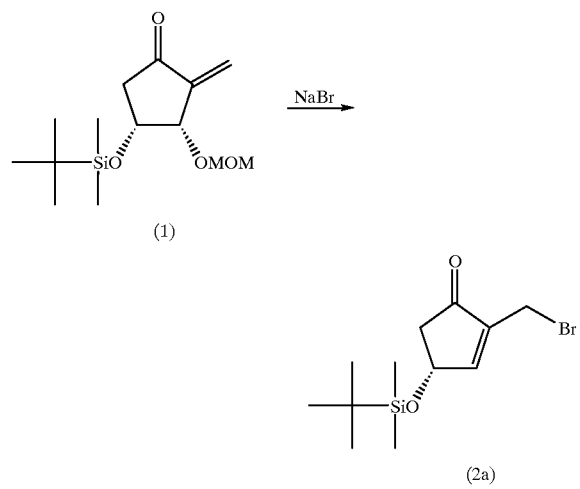

In a dry nitrogen atmosphere, boron trifluoride diethyl ether complex (1.24 ml, 10.1 mmol) was added to a solution of an enone (1) (2.16 g, 7.54 mmol) and NaBr (1.73 g, 16.8 mmol) in dry acetone (28 ml) at room temperature and stirred for 1½ hours at room temperature. The reaction solution was poured into ether (10 ml) and saturated aqueous sodium bicarbonate solution (10 ml). After the aqueous layer was extracted with ether (10 ml) again, the organic layer was washed with aqueous sodium thiosulfate solution and dried over anhydrous magnesium sulfate, and the solvent was distilled off in vacuum. The residue was purified by silica gel column chromatography, obtaining an end compound (2a) in an amount of 2.04 g (yield 89%). Analytical data of compound (2a) are shown below.

$^1$H-NMR (300 MHz, CDCl$_3$CHCl$_3$) δ7.38–7.41 (m, 1H), 4.91–4.97 (m, 1H), 4.02 (s, 2H), 2.83 (dd, J=6.0, 18.0 Hz, 1H), 2.36 (dd, J=18.0, 2.2 Hz, 1H), 0.90 (s, 9H), 0.12 and 0.14 (2s, 6H)

$^{13}$C-NMR (75 MHz, CDCl$_3$) δ202.8, 160.5, 142.9, 68.6, 45.6, 25.9, 21.0, 18.1, −4.7 (2C)

IR (neat) 2930, 2852, 1710, 1460, 1342, 1250, 1082, 906, 830, 775

$[\alpha]^{23}{}_D$+26.3 (c 0.96, CHCl$_3$)

EXAMPLE 2

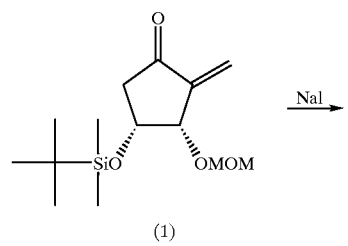

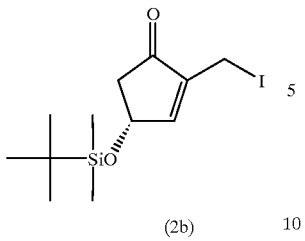

(2b)

In a dry nitrogen atmosphere, boron trifluaride diethyl ether complex (0.87 ml, 7.08 mmol) was added to a solution of an enone (1) (1.30 g, 4.54 mmol) and NaI (1.77 g, 11.8 mmol) in dry acetone (20 ml) at room temperature and stirred for 1½ hours at room temperature. The reaction solution was poured into ether (10 ml) and saturated aqueous sodium bicarbonate solution (10 ml). After the aqueous layer was extracted with ether (10 ml) again, the organic layer was washed with aqueous sodium thiosulfate solution and dried over anhydrous magnesium sulfate, and the solvent was distilled off in vacuum. The residue was purified by silica gel column chromatography, obtaining 1.02 g (yield 64%) of an end compound (2b). Analytical data of compound (2b) are shown below.

$^1$H-NMR (300 MHz, CDCl$_3$, CHCl$_3$) δ7.38 (d, J=2.5 Hz, 1H), 4.83–4.90 (m, 1H), 3.91 (s, 2H), 2.83 (dd, J=6.0, 18.4 Hz, 1H), 2.34 (dd, J=2.2, 18.4 Hz, 1H), 0.91 (s, 9H), 0.12 and 0.13 (2s, 6H)

EXAMPLES 3–7

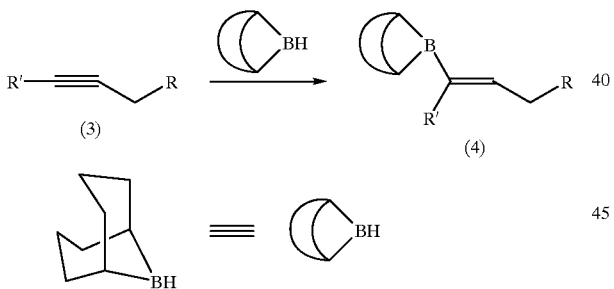

In a dry nitrogen atmosphere, a THF solution of 9-BBN (0.5M×4 ml=2 mmol) was slowly added to an acetylene (3) (2 mmol) in dry THF (0.5 ml) at 0° C. The solution was stirred for more than 12 hours at room temperature, obtaining a THF solution of a compound (4).

4a: R=nC$_5$H$_{11}$, R'=H

4b: R=CH$_2$CH$_2$CO$_2$Me, R'=H

4c: R=nC$_5$H$_{11}$, R'=SiMe$_3$

4d: R=CH$_2$CH$_2$CO$_2$Me, R'=SiMe$_3$

4e: R=CH═CHCO$_2$Me, R'=SiMe$_3$

EXAMPLES 8–9

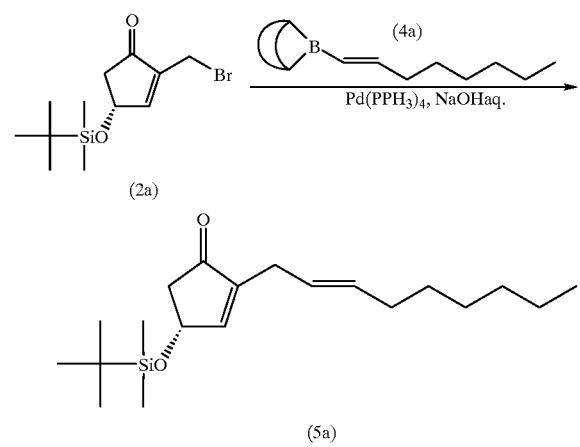

In a dry nitrogen atmosphere, 3.3 ml o( borane-THF complex (1 M) was ice cooled, and 0.66 ml (6.6 mmol) of cycohexene was slowly added dropwise thereto and stirred at the temperature for 1½ hours. Under ice cooling, an acetylene (3) (3 mmol) in dry THF (4 ml) was slowly added thereto and stirred at the temperature for 20 minutes. The reaction mixture was stirred for 1 hour at room temperature, obtaining a THF solution of a compound (4').

4'd: R=CH$_2$CH$_2$CO$_2$Me, R'=SiMe$_3$

4'e: R=CH═CHCO$_2$Me, R'=SiMe$_3$

EXAMPLE 10

In a dry nitrogen atmosphere, Pd(PPh$_3$)$_4$ (5.8 mg, 5 mol %) was added to an enone (2a) (30.5 mg, 0.1 mmol) in dry benzene and stirred for 10 minutes. A solution of the above-obtained compound (4a) wherein R═nC$_5$H$_{11}$ and R'═H in THF (0.4M×0.5 ml=0.2 mmol) and an aqueous NaOH solution (2M×0.2 ml=0.4 mmol) were added thereto. The reaction mixture was heated under reflux for 2 hours. The reaction mixture was cooled to room temperature again, whereupon hexane (1 ml) and aqueous ammonium chloride solution (1 ml) were added thereto. After extraction, the organic layer was dried over anhydrous magnesium sulfate, and the solvent was distilled off under vacuum. The residue was purified by silica gel column chromatography, obtaining an end compound (5a) in an amount of 21.7 mg (yield 65%). Analytical data of compound (5a) are shown below.

$^1$H-NMR (300 MHz, CDCl$_3$, CHCl$_3$) δ7.03 (br, s, 1H), 5.37–5.58 (m, 2H), 4.86–4.93 (m, 1H), 2.86 (d, J=5.4 Hz, 1H), 2.79 (dd, J=4.8, 14.4 Hz, 1H), 2.29 (d, J=14.4 Hz, 1H), 2.01 (dt, J=6.8, 5.4 Hz, 1H), 1.12–1.68 (m, 8H), 0.84–0.92 (m, 3H), 0.91 (s, 9H), 0.11 and 0.13 (2s, 6H)

EXAMPLE 11

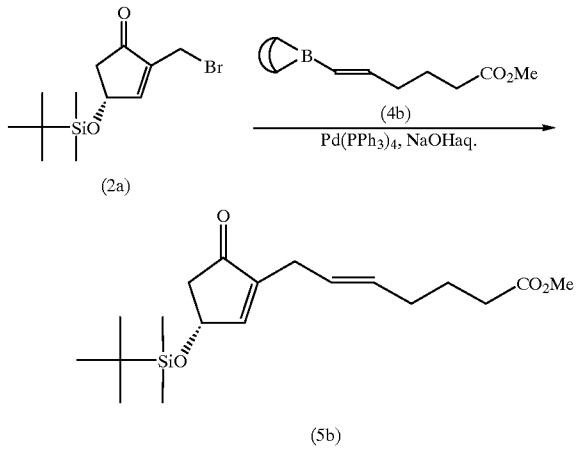

(2a)

(5b)

In a dry nitrogen atmosphere, Pd(PPh$_3$)$_4$ (5.8 mg 5 mol %) was added to an enone (2a) (30.5 mg, 0.1 mmol) in dry benzene and stirred for 10 minutes. A solution of the above-obtained compound (4b) wherein R=CH$_2$CH$_2$CO$_3$Me and R'=H in THF (0.4M×0.5 ml=0.2 mmol) and an aqueous NaOH solution (4M×0.2 ml=0.8 mmol) were added thereto. The reaction mixture was heated under reflux for 4 hours. The reaction mixture was cooled to room temperature again, diluted with ether (2 ml), and adjusted to pH 6 with an aqueous solution of 1N HCl. After extraction, the organic layer was washed with saturated aqueous sodium chloride solution and dried over anhydrous magnesium sulfate, and the solvent was distilled off under vacuum. The residue was quantitatively determined by $^1$H-NNR spectroscopy (internal standard: mesitylene), obtaining an end compound (5b) in a yield of 48%. Analytical data of compound (5b) are shown below.

$^1$H-NMR (300 MHz, CDCl$_3$, CHCl$_3$) δ7.05 (br, s, 1H), 5.41–5.53 (m, 2H), 4.86–4.92 (m, 1H), 3.67 (s, 3H), 2.87 (br, s, 2H), 2.76 (dd, J=4.8, 15.0 Hz, 1H), 2.24–2.41 (m, 5H), 2.02–2.13 (m, 2H), 0.91 (s, 9H), 0.12 (s, –6H)

EXAMPLE 12

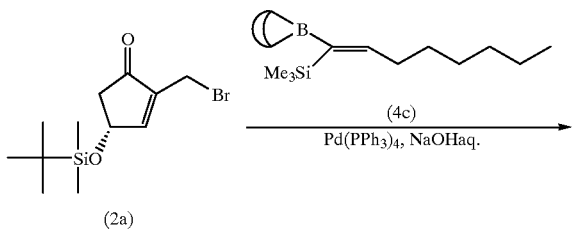

(2a)

(5c)

As in Example 11, a compound (5c) was obtained using a compound (4c) wherein R=nC$_5$H$_{11}$ and R'=SiMe$_3$. Analytical data of compound (5c) are shown below.

$^1$H-NMR (300 MHz, CDCl$_3$, CHCl$_3$) δ6.92 (br, s, 1H), 5.99 (t, J=6.3 Hz, 1H), 4.82–4.94 (m, 1H), 2.89 (br, s, 1H), 2.76 (dd, J=4.8, 15.0 Hz, 1H), 2.30 (d, J=15.0 Hz, 1H), 2.02–2.25 (m, 2H), 1.20–1.95 (m, 8H), 0.84–0.06 (m, 3H), 0.91 (s, 9H), 0.11 (s, 6H)

EXAMPLE 13

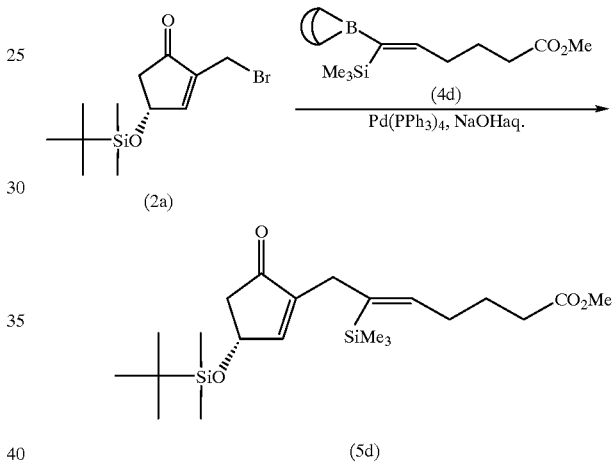

(2a)

(5d)

In a dry nitrogen atmosphere, Pd(PPh$_3$)$_4$ (5.8 mg, 5 mol %) was added to an enone (2a) (30.5 mg, 0.1 mmol) in dry benzene and stirred for 10 minutes. A solution of the above-obtained compound (4d) wherein R=CH$_2$CH$_2$COOMe and R'=SiMe$_3$ in THF (0.4M×0.5 ml=0.2 mmol) and an aqueous NaOH solution (4M×0.2 ml=0.8 mmol) were added thereto. The reaction mixture was heated under reflux for 4 hours. The reaction mixture was cooled to room temperature again, diluted with ether (2 ml), and adjusted to pH 6 with an aqueous solution of 1N HCl. After extraction, the organic layer was washed with saturated sodium chloride solution and dried over anhydrous magnesium sulfate, and the solvent was distilled off under vacuum. The residue was purified by silica gel column chromatography and quantitatively determined by $^1$H-NMR spectroscopy (internal standard: mesitylene), obtaining an end compound (5d) in a yield of 62%. Analytical data of compound (5d) are shown below.

$^1$H-NMR (300 MHz, CDCl$_3$, CHCl$_3$) δ6.88–6.93 (m, 1H), 5.93 (t, J=7.20 Hz, 1H), 4.82–4.88 (m, 1H), 3.67 (s, 3H), 2.80–2.95 (m, 2H), 2.74 (dd, J=18.3, 5.9 Hz, 1H), 2.33 (t, J=7.5 Hz, 1H), 2.15–2.25 (m, 3H), 1.65–1.77 (m, 2H), 0.89 (s, 9H), 0.08 (s, 9H), 0.09 and 0.11 (2s, 6H)

$^{13}$C-NMR (75 MHz, CDCl$_3$) δ205.5, 173.8, 157.8, 147.2, 144.6, 136.4, 68.7, 51.5, 45.7, 33.5, 32.8, 31.3, 25.7, 25.1, 18.0, 0.13 (3C), –4.71 (2C)

IR (neat) 2960, 2852, 1710, 1435, 1350, 1248, 1160, 1078, 835, 775

$[\alpha]^{23}_D$ +5.54 (c 1.03, CHCl$_3$)

EXAMPLE 14

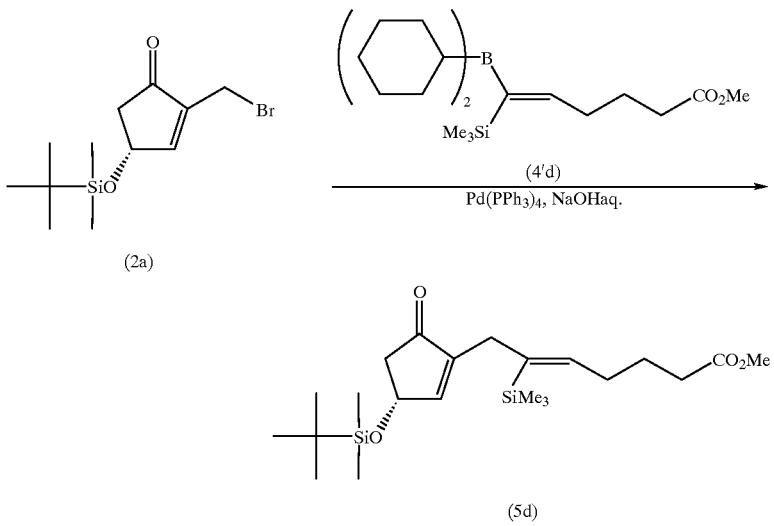

In a dry nitrogen atmosphere, Pd(PPh$_3$)$_4$ (94.7 mg, 5 mol %) was added to an enone (2a) (500 mg, 1.64 mmol) in 16.4 ml of dry benzene and stirred for 10 minutes. A solution of the above-obtained compound (4'd) wherein R=CH$_2$CH$_2$CO$_3$Me and R'=SiMe$_3$ in THF (0.35M×8.56 ml=3 mmol) and an aqueous NaOH solution (3M×1.1 ml=3.3 mmol) were added thereto. The reaction mixture was heated under reflux for 1½ hours. The reaction mixture was cooled to room temperature again, diluted with ether (2 ml), and adjusted to pH 6 with an aqueous solution of 1N HCl. After extraction, the organic layer was washed with saturated sodium chloride solution and dried over anhydrous magnesium sulfate. The solvent was distilled off under vacuum, obtaining an end compound (5d) in an amount of 2.20 g (yield 92%).

EXAMPLE 15

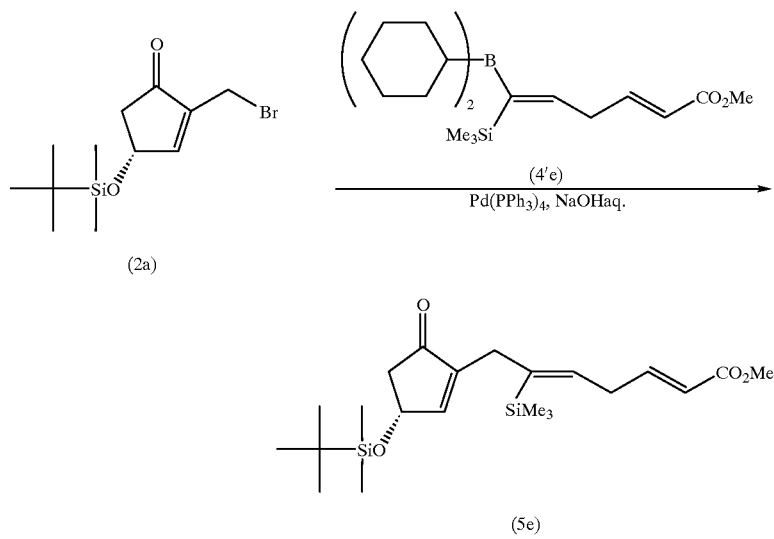

In a dry nitrogen atmosphere, Pd(PPh$_3$)$_4$ (102 mg, 3 mol %) was added to an enone (2a) (900 mg, 2.94 mmol) in dry benzene and stirred for 10 minutes. A solution of the above-obtained compound (4'e) wherein R=CH=CHCOOMe and R'=SiMe$_3$ in THF (0.35M×11.3 ml=4.0 mmol) and an aqueous NaOH solution (3M×2.7 ml=8.0 mmol) were added thereto. The reaction mixture was heated under reflux for 30 minutes. The reaction mixture was cooled to room temperature again, diluted with ether, and adjusted to pH 6 with an aqueous solution of 1N HCl. After extraction, the organic layer was washed with saturated aqueous sodium bicarbonate and dried over anhydrous magnesium sulfate. The solvent was distilled off under vacuum, obtaining an end compound (5e). Analytical data of compound (5e) are shown below.

$^1$H-NMR (300 MHz, CDCl$_3$, CHCl$_3$) δ6.96 (dt, J=15.7, 6.2 Hz, 1H), 6.89–6.94 (m, 1H), 5.94 (t, J=7.5 Hz, 1H), 5.83 (dt, J=15.7, 1.7 Hz, 1H), 4.81–4.92 (m, 1H), 3.72 (s, 3H), 3.03–3.11 (m, 2H), 2.88–3.01 (m, 2H), 2.75 (dd, J=5.9, 18.3 Hz, 1H), 2.28 (dd, J=2.0, 18.3 Hz, 1H), 0.88 (S, 9H), 0.09 and 0.10 (2s, 15H)

$^{13}$C-NMR (75 MHz, CDCl$_3$) δ205.4, 166.8, 158.0, 146.7, 146.6, 139.4, 139.1, 121.5, 68.7, 51.4, 45.6, 34.5, 32.7, 25.7, 18.0, 0.09 (3C), −4.7 (2C)

IR (neat) 2930, 2870, 1718, 1660, 1620, 1470, 1440, 1410, 1350, 1330, 1260, 1200, 1170, 1080, 1010, 910, 840, 780, 760

$[\alpha]^{23}_D$+2.14 (c 0.58, CHCl$_3$)

EXAMPLES 16–17

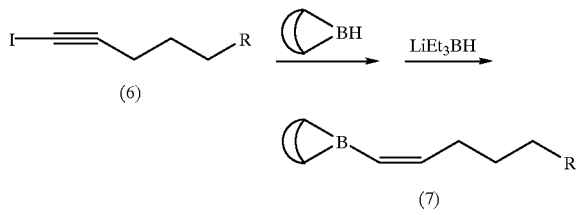

In a dry nitrogen atmosphere, a THF solution of 9-BBN (0.5M×4 ml=2 mmol) was slowly added to 1-iodo-1-acetylene (6) (2 mmol) in dry THF (0.5 ml) at 0° C. The solution was stirred at room temperature for more than 12 hours and then cooled to −78° C., and a THF solution of lithium triethylborohydride (1.0M×2 ml=2 mmol) was added thereto. The mixture was heated up to room temperature over more than 3 hours, obtaining a THF solution of a compound (7).

7a: R=nC$_5$H$_{11}$
7b: R=CH$_2$CH$_2$CO$_2$Me

EXAMPLE 18

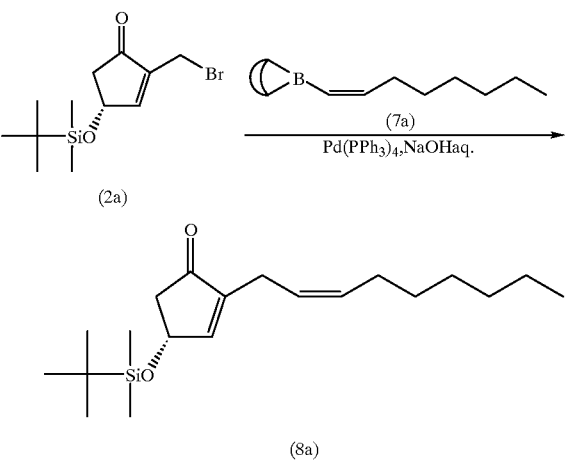

In a dry nitrogen atmosphere, Pd(PPh$_3$)$_4$ (5.8 mg, 5 mol %) was added to an enone (2a) (30.5 mg, 0.1 mmol) in dry benzene and stirred for 10 minutes. A solution of the above-obtained compound (7a) (R=nC$_5$H$_{11}$) in THF (0.29M×2 ml=0.58 mmol) and an aqueous NaOH solution (2M×0.3 ml=0.6 mmol) were stirred for 1 minute, with the aqueous layer separated off, and added thereto. The reaction mixture was combined with an aqueous NaOH solution (2M×0.2 ml=0.4 mmol) and heated under reflux for 2 hours. The reaction mixture was cooled to room temperature again, and hexane (1 ml) and aqueous ammonium chloride solution (1 ml) were added thereto. After extraction, the organic layer was dried over anhydrous magnesium sulfate, and the solvent was distilled off under vacuum. The residue was purified by silica gel column chromatography, obtaining an end compound (8a) in an amount of 20.6 mg (yield 61%). Analytical data of compound (8a) are shown below.

$^1$H-NMR (300 MHz, CDCl$_3$, CHCl$_3$) δ7.03 (br, s, 1H), 5.30–5.68 (m, 2H), 4.82–4.93 (m, 1H), 2.91 (d, J=7.1 Hz, 1H), 2.76 (dd, J=5.9, 18.2 Hz, 1H), 2.29 (dd, J=2.1, 18.2 Hz, 1H), 2.04 (dt, J=6.8, 7.1 Hz, 1H), 1.17–1.65 (m, 8H), 0.91 (s, 9H), 0.88 (t, J=6.0 Hz, 3H), 0.11 and 0.12 (2s, 6H)

EXAMPLE 19

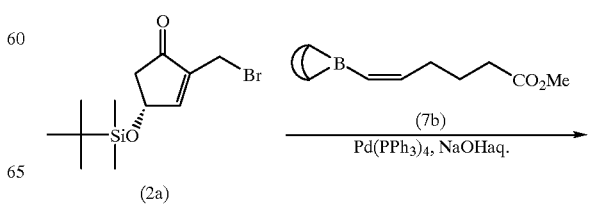

-continued

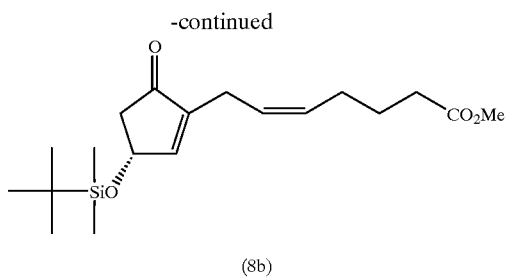

(8b)

In a dry nitrogen atmosphere, Pd(PPh$_3$)$_4$ (5.8 mg, 5 mol %) was added to an enone (2a) (30.5 mg, 0.1 mmol) in dry benzene and stirred for 10 minutes. A solution of the above-obtained compound (7b) wherein R=CH$_2$CH$_2$CO$_2$Me in THF (0.29M×0.73 ml=0.21 mmol) and an aqueous NaOH solution (4M×0.3 ml=1.2 mmol) were stirred for 1 minute, with the aqueous layer separated off, and added thereto. The reaction mixture was combined with an aqueous NaOH solution (4M×0.2 ml=0.8 mmol) and heated under reflux for 2 hours. The reaction mixture was cooled to room temperature again, diluted with ether (2 ml), and adjusted to pH 6 with an aqueous solution of 1N HCl. After extraction, the organic layer was washed with saturated aqueous sodium chloride solution and dried over anhydrous magnesium sulfate, and the solvent was distilled off under vacuum. The residue was quantitatively determined by $^1$H-NMR spectroscopy (internal standard: mesitylene), obtaining an end compound (8b) in a yield of 23%. Analytical data of compound (8b) are shown below.

$^1$H-NMR (300 MHz, CDCl$_3$, CHCl$_3$) δ7.09 (br, s, 1H), 5.45–5.51 (m, 2H), 4.87 (m, 1H), 3.69 (s, 3H), 2.88 (br, s, 1H), 2.73 (dd, J=4.9, 15 Hz, 1H), 2.18–2.45 (m, 5H), 0.91 (s, 9H), 0.11 (s, 6H)

EXAMPLE 20

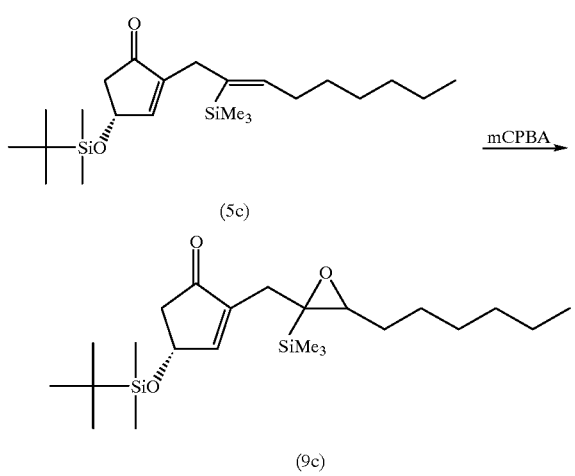

In a dry nitrogen atmosphere, 13.6 mg (0.079 mmol) of meta-chloroperbenzoic acid (mCPBA) was added to a compound (5c) (10 mg, 0.026 mmol) in dry methylene chloride under ice cooling. After restoration to room temperature, the mixture was stirred for 12 hours at room temperature. Reaction was terminated with aqueous sodium bicarbonate. After extraction with diethyl ether, the organic layer was washed with saturated aqueous sodium chloride solution and dried over anhydrous magnesium sulfate, and the solvent was distilled off under vacuum. Analysis of the residue by $^1$H-NMR spectroscopy confirmed an end compound (9c). Analytical data of compound (9c) are shown below.

$^1$H-NMR (300 MHz, CDCl$_3$, CHCl$_3$) δ7.21 (br, s, 1H), 4.88 (m, 1H), 2.64–2.81 (m, 3H), 2.39 (t, J=7.6 Hz, 1H), 2.01–2.34 (m, 1H), 1.05–1.73 (m, 10H), 0.80–0.99 (m, 3H), 0.91 (s, 9H), 0.10, 0.12, 0.13 (3s, 15H)

EXAMPLE 21

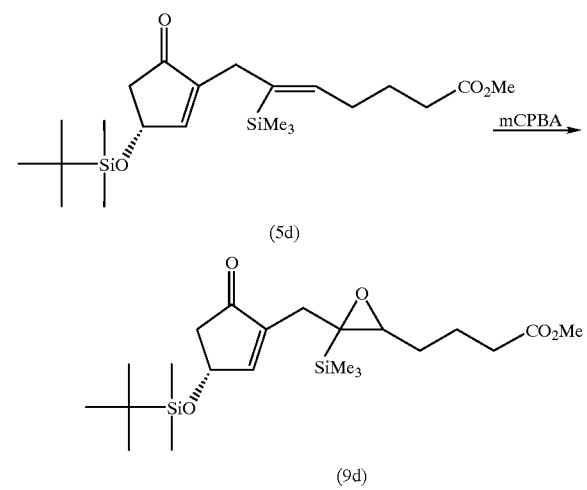

In a dry nitrogen atmosphere, 170 mg (0.981 mmol) of meta-chloroperbenzoic acid (MCPBA) was added to a compound (5d) (150 mg, 0.353 mmol) in dry methylene chloride under ice cooling. After restoration to room temperature, the mixture was stirred for 4 hours at room temperature. Reaction was terminated with aqueous sodium bicarbonate. After extraction with diethyl ether, the organic layer was washed with saturated aqueous sodium chloride solution and dried over anhydrous magnesium sulfate, and the solvent was distilled off under vacuum. The residue was quantitatively determined by $^1$H-NMR spectroscopy (internal standard: Trichlene), obtaining an end compound (9d) in a yield of 95%. Analytical data of compound (9d) are shown below.

$^1$H-NMR (300 MHz, CDCl$_3$, CHCl$_3$) δ7.16–7.22 (m, 1H), 4.83–4.91 (m, 1H), 3.67 (s, 3H), 1.60–1.90 (m, 5H), 1.55–1.89 (m, 4H), 1.10–1.55 (m, 7H), 0.89 (s, 9H), 0.08–0.15 (m, 15H)

EXAMPLE 22

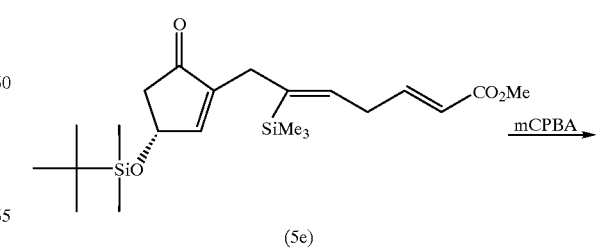

-continued

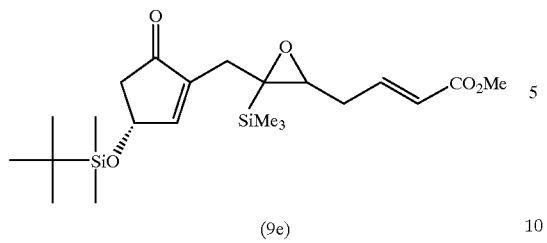

(9e)

To a compound (5e) (synthesized from 900 mg of compound (2a) in Example 15, starting with 2.94 mmol) in dry methylene chloride under ice cooling were added 2 ml of 35% hydrogen peroxide and 2.0 ml (0.981 mmol) of a saturated aqueous solution of 3N sodium hydroxide. After restoration to room temperature, the mixture was stirred for 4 hours at room temperature. After extraction with diethyl ether, the organic layer was washed with 1N hydrochloric acid and saturated aqueous sodium chloride solution and dried over anhydrous magnesium sulfate, and the solvent was distilled off under vacuum. The residue was purified by silica gel column chromatography, obtaining an end compound (9e) in an amount of 1.01 g (two-step yield 81%). Analytical data of compound (9e) are shown below.

$^1$H-NMR (300 MHz, CDCl$_3$) δ7.16–7.20 (m, 1H), 6.78–7.05 (m, 1H), 5.80–6.02 (m, 1H), 4.85–4.93 (m, 1H), 3.73 (s, 3H), 2.65–2.95 (m, 2H), 2.10–2.60 (m, 5H), 0.89 (s, 9H), 0.08–0.18 (m, 15H)

EXAMPLE 23

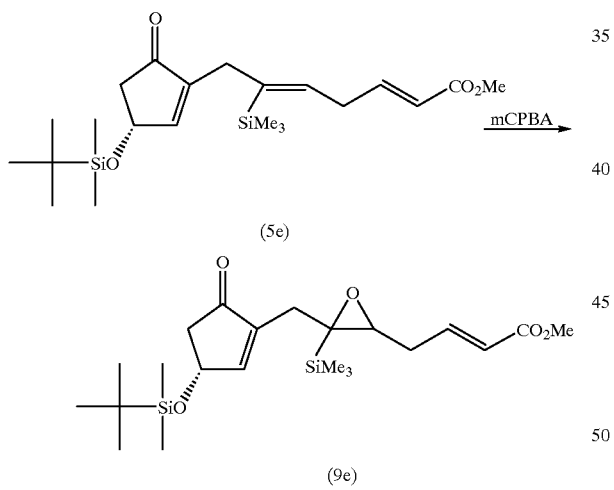

In a dry nitrogen atmosphere, 30 mg (0.177 mmol) of meta-chloroperbenzoic acid (mCPBA) was added to a compound (5e) (50 mg, 0.118 mmol) in dry methylene chloride under ice cooling. After restoration to room temperature, the mixture was stirred for 4 hours at room temperature. Reaction was terminated with aqueous sodium bicarbonate. After extraction with diethyl ether, the organic layer was washed with saturated aqueous sodium chloride solution and dried over anhydrous magnesium sulfate, and the solvent was distilled off under vacuum. The residue was quantitatively determined by $^1$H-NMR spectroscopy (internal standard: Trichlene), obtaining an end compound (9e) in a yield of 81%.

EXAMPLE 24

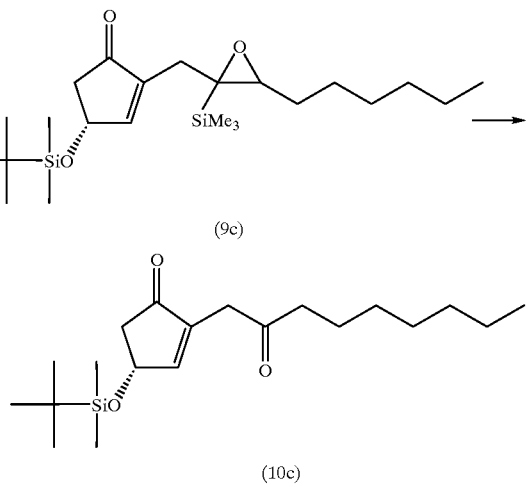

About 20 mg (0.14 mmol) of boron trifluoride diethyl ether complex was added to a compound (9c) (about 10 mg, 0.026 mmol) in MeOH (1 ml) under ice cooling, which was stirred for 20 minutes. Reaction was terminated with saturated aqueous sodium bicarbonate. The reaction solution was dried over anhydrous sodium sulfate, filtered, and washed with diethyl ether, and the solvent was distilled off under vacuum. Analysis of the residue by $^1$H-NMR spectroscopy confirmed an end compound (10c). Analytical data of compound (10c) are shown below.

$^1$H-NMR (300 MHz, CDCl$_3$, CHCl$_3$) δ7.32 (br, s, 1H), 4.94–5.00 (m, 1H), 3.18–3.45 (m, 2H), 2.76 (dd, J=6.0, 18.3 Hz, 1H), 2.48 (t, J=7.1 Hz, 2H), 2.27 (dd, J=2.1, 18.3 Hz, 1H), 1.05–1.89 (m, 10H), 0.80–0.98 (m, 3H), 0.90 (s, 9H), 0.13, 0.14 (2s, 6H)

EXAMPLE 25

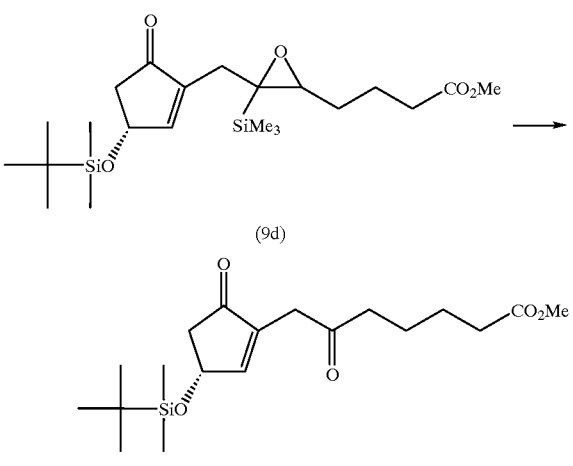

About 20 mg (0.14 mmol) of boron trifluoride diethyl ether complex was added to a compound (9d) (86 mg, 0.195 mmol) in MeOH (3.9 ml) under ice cooling, which was stirred for 10 minutes. Reaction was terminated with saturated aqueous sodium bicarbonate. After extraction with diethyl ether, the organic layer was washed with saturated aqueous sodium chloride solution and dried over anhydrous magnesium sulfate, and the solvent was distilled off under vacuum. The residue was purified by silica gel column chromatography, obtaining an end compound (10d) in an amount of 54.3 mg (yield 76%). Analytical data of compound (10d) are shown below.

$^1$H-NMR (300 MHz, CDCl$_3$, CHCl$_3$) δ7.30–7.32 (m, 1H), 4.94–4.99 (m, 1H), 3.65 (s, 3H), 3.39 (d, J=17.3 Hz, 1H), 3.22 (d, J=17.3 Hz, 1H), 2.76 (dd, J=18.3, 5.9 Hz, 1H), 2.48–2.55 (m, 2H), 2.26–2.36 (m, 2H), 2.27 (dd, J=18.3, 2.1 Hz, 1H), 1.55–1.70 (m, 4H), 0.90 (s, 9H), 0.11 and 0.12 (2s, 6H)

$^{13}$C-NMR (75 MHz, CDCl$_3$) δ205.6, 205.2, 173.7, 160.3, 139.4, 69.2, 51.5, 44.7, 42.6, 37.7, 33.7, 24.3, 23.0, 25.8, 18.1, −4.7 (2C)

IR (neat) 2940, 2850, 1710, 1630, 1455, 1430, 1400, 1340, 1240, 1190, 1160, 1079, 960, 906, 828, 768

$[\alpha]^{23}_D$ −3.90 (c 0.93, CHCl$_3$)

EXAMPLE 26

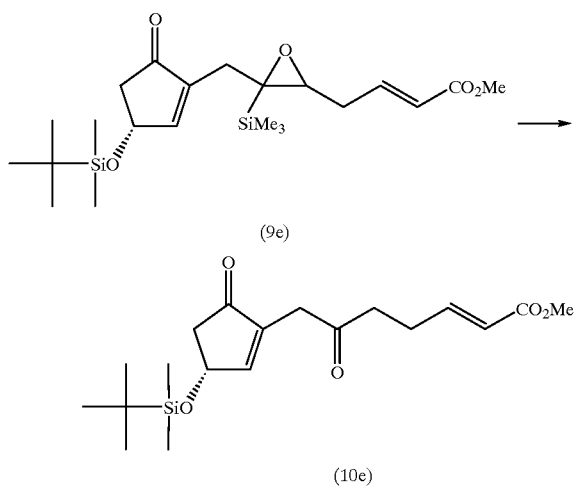

About 60 mg (0.45 mmol) of boron trifluoride diethyl ether complex was added to a compound (9e) (771 mg, 2.10 mmol) in MeOH (21 ml) under ice cooling, which was stirred for 30 minutes. Reaction was terminated with saturated aqueous sodium bicarbonate. After extraction with ethyl acetate, the organic layer was washed with saturated aqueous sodium chloride solution and dried over anhydrous magnesium sulfate, and the solvent was distilled off under vacuum. The residue was purified by silica gel column chromatography, obtaining an end compound (10e) in an amount of 546 mg (yield 71%). Analytical data of compound (10e) are shown below.

$^1$H-NMR (300 MHz, CDCl$_3$, CHCl$_3$) δ7.28–7.39 (m, 1H), 6.90 (dt, J=15.7, 6.8 Hz, 1H), 5.82 (dt, J=15.7, 1.6 Hz, 1H), 4.93–5.04 (m, 1H), 3.71 (s, 3H), 3.41 (d, J=17.2 Hz, 1H), 3.23 (d, J=17.2 Hz, 1H), 2.76 (dd, J=18.3, 5.9 Hz, 1H), 2.62–2.70 (m, 2H), 2.42–2.54 (m, 1H), 2.17 (dd, J=18.3, 2.1 Hz, 1H), 0.89 (s, 9H), 0.11 and 0.12 (2s, 6H)

$^{13}$C-NMR (75 MHz, CDCl$_3$) δ205.1, 204.2, 166.8, 160.5, 147.1, 139.2, 121.8, 69.2, 51.4, 44.7, 40.9, 37.8, 25.9, 25.8, 18.1, −4.7 (2C)

IR (neat) 2930, 2860, 1710, 1660, 1420, 1350, 1280, 1250, 1200, 1170, 1080, 970, 905, 820, 780

$[\alpha]^{23}_D$ +3.89 (c 0.72, CHCl$_3$)

REFERENCE EXAMPLE

Compound (10) is important as an intermediate for the synthesis of 6-keto-PGE's. The synthesis of PGE's from this intermediate may be in accord with the process of JP-A 228933/1989. Examples are illustrated below.

Reference Example 1

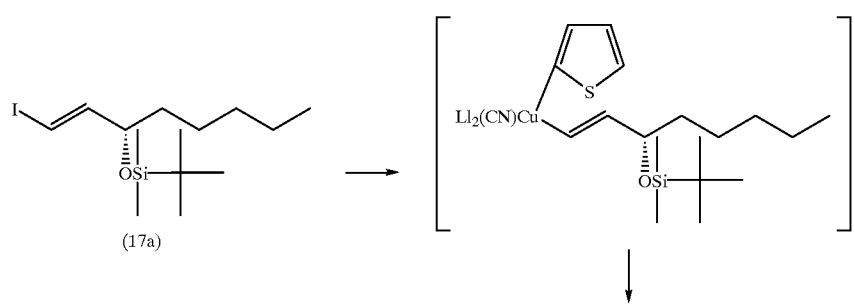

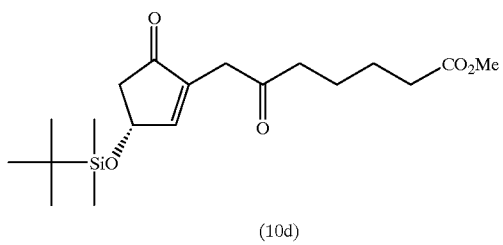

(10d)

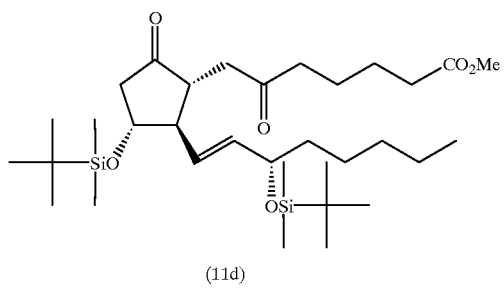

(11d)

In a dry nitrogen atmosphere, 1 ml of a diethyl ether solution containing 100 mg (0.271 mmol) of compound (17a) was stirred, 0.32 ml (0.543 mmol, concentration in pentane 1.7 M) of t-BuLi was added thereto at −78° C., and the mixture was stirred for 30 minutes at the temperature. Next, 1.25 ml (0.313 mmol, concentration in tetrahydrofuran 0.25 M) of lithium 2-thienylcyanocuprate was added thereto, and the mixture was stirred for 30 minutes at −78° C. Moreover, a tetrahydrofuran solution containing 50 mg (0.136 mmol) of compound (10d) was added dropwise to the mixture at −78° C. The mixture was warmed up to room temperature in 1 hours. Reaction was terminated with saturated aqueous ammonium chloride solution. With diethyl ether added, the reaction solution was stirred for 1 hour at room temperature. After the organic layer was separated, the aqueous layer was further extracted with hexane. The organic layer was dried over magnesium sulfate, concentrated, and then purified by silica gel column chromatography, obtaining compound (11d) in an amount of 62 mg (0.101 mmol, yield 75%). Analytical data of compound (11d) are shown below.

$^1$H-NMR (300 MHz, CDCl$_3$, CHCl$_3$) δ5.55 (dd, J=15.6, 4.6 Hz, 1H), 5.47 (dd, J=15.6, 6.6 Hz, 1H), 4.02–4.13 (m, 2H), 3.66 (s, 3H), 2.15–2.73 (m, 2H), 1.10–1.73 (m, 12H), 0.86–0.88 (m, 21H), 0.03 and 0.04 (2s, 12H)

$^{13}$C-NMR (75 MHz, CDCl$_3$) δ214.2, 207.5, 173.7, 137.0, 128.3, 73.3, 72.5, 53.0, 51.5, 49.8, 46.7, 42.4, 39.9, 38.5, 33.8, 31.8, 25.8, 25.9, 25.0, 24.4, 23.1, 22.6, 14.0, 18.0, 18.2, −4.74, −4.68, −4.58, −4.29 (4C)

IR (neat) 2925, 2850, 1745, 1720, 1250, 1155, 1100, 1000, 965, 935, 865, 835, 805, 775

$[\alpha]^{21}_D$ −38.6 (c 0.46, CHCl$_3$)$_{13}$

This compound is known in the literature. Therefore, we succeeded in formal overall synthesis of 6-keto-PGE$_1$.

Reference Example 2

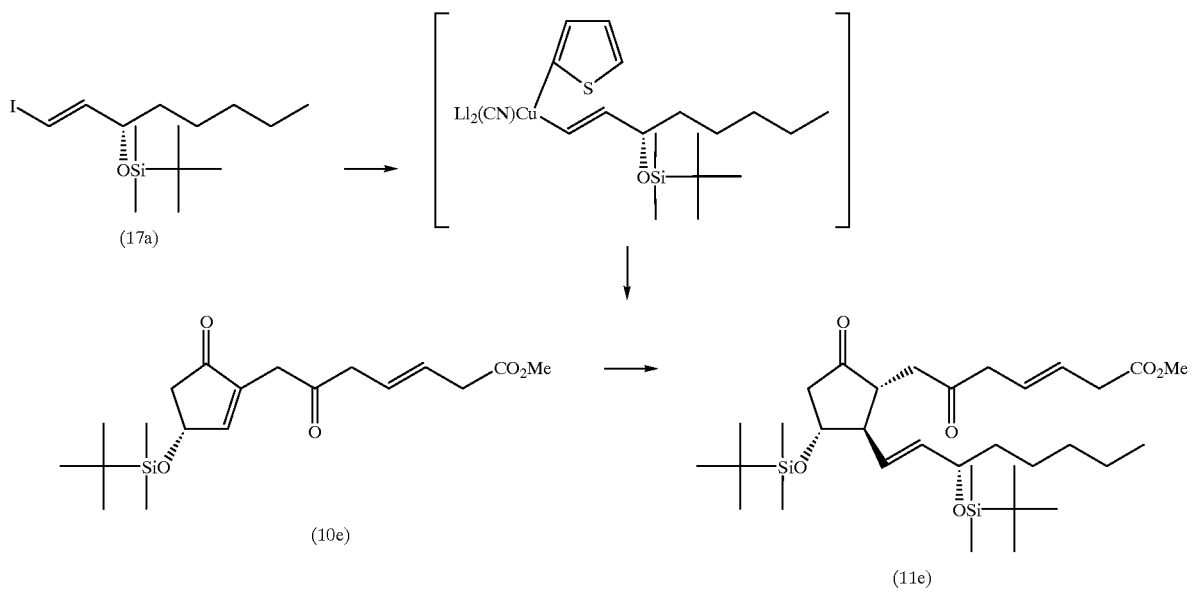

(17a)

(10e)

(11e)

In a dry nitrogen atmosphere, 4.1 ml of a diethyl ether solution containing 151 mg (0.410 mmol) of compound (17a) was stirred, 0.45 ml (0.765 mmol, concentration in pentane 1.7 M) of t-BuLi was added thereto at −78° C., and the mixture was stirred for 30 minutes at the temperature. Next, 1.96 ml (0.491 mmol, concentration in tetrahydrofuran 0.25 M) of lithium 2-thienylcyanocuprate was added thereto, and the mixture was stirred for 30 minutes at −78° C. Moreover, 1 ml of a diethyl ether solution containing 27 mg (0.0737 mmol) of compound (10e) was added dropwise to the mixture at −78° C. The mixture was warmed up to −30° C. in 1 hours. Reaction was terminated with saturated aqueous ammonium chloride solution. With diethyl ether added, the reaction solution was stirred for 1 hour at room temperature. After the organic layer was separated, the aqueous layer was further extracted with diethyl ether. The organic layer was dried over magnesium sulfate, concentrated, and then purified by silica gel column chromatography, obtaining compound (11e) in an amount of 33.4 mg (yield 76%). Analytical data of compound (11e) are shown below.

$^1$H-NMR (300 MHz, CDCl$_3$, CHCl$_3$) δ6.91 (dt, J=15.7, 6.5 Hz, 1H), 5.81 (d, J=15.7 Hz, 1H), 5.55 (dd, J=15.4, 4.4 Hz, 1H), 5.47 (dd, J=15.4, 6.6 Hz, 1H), 4.03–4.14 (m, 2H), 3.71 (s, 3H), 2.25–2.75 (m, 10H), 1.15–1.50 (m, 8H), 0.86–0.88 (m, 2H), 0.03 and 0.04 (s, 12H)

$^{13}$C-NMR (75 MHz, CDCl$_3$) δ214.0, 206.0, 166.7, 147.2, 137.1, 128.1, 121.7, 73.2, 72.5, 53.1, 51.4, 49.9, 46.6, 40.8, 39.8, 38.4, 31.8, 25.9, 25.7, 25.0, 22.6, 18.0, 18.2, 14.0, −4.75, −4.70, −4.60, −4.30 (4C)

IR (neat) 2930, 2860, 1720, 1660, 1485, 1440, 1410, 1370, 1260, 1160, 1100, 1010, 970, 870, 840, 780

$[\alpha]^{21}_D$ −43.4 (c 0.67, CDCl$_3$)

Reference Example 3

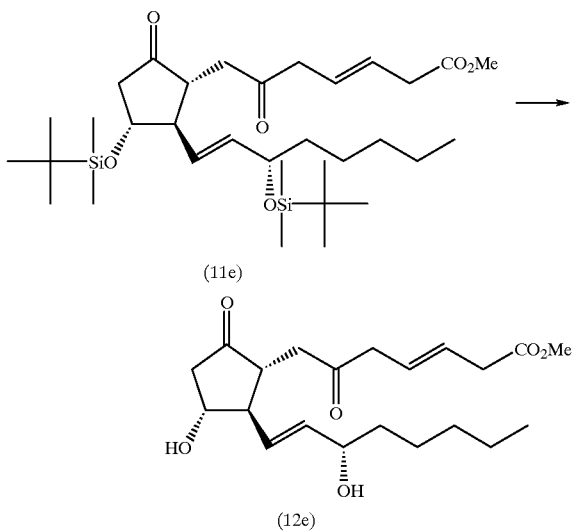

(11e)

(12e)

In a dry nitrogen atmosphere, 1.9 ml of an acetonitrile solution containing 34 mg (0.0558 mmol) of compound (11e) and 0.11 ml of pyridine was stirred, 0.1 ml (about 70 mg, about 3.5 mmol) of hydrogen fluoride pyridine complex (containing about 70% of hydrogen fluoride) was added thereto at 0° C., and the mixture was allowed to warm up to room temperature. Stirring was continued for 4 hours at room temperature. Reaction was terminated with saturated aqueous sodium bicarbonate and ethyl acetate was added. The aqueous layer was saturated with ammonium sulfate, the organic layer was separated, and the aqueous layer was further extracted with ethyl acetate. The organic layer was dried over magnesium sulfate, concentrated, and then purified by silica gel column chromatography, obtaining compound (12e) in an amount of 20.4 mg (0.0536 mmol, yield 96%). Analytical data of compound (12e) are shown below.

$^1$H-NMR (300 MHz, CDCl$_3$, (CH$_3$)$_4$Si) δ6.90 (dt, J=15.7, 6.6 Hz, 1H), 5.81 (d, J=15.7 Hz, 1H), 5.61 (dd, J=15.2, 6.6 Hz, 1H), 5.51 (dd, J=15.2, 7.8 Hz, 1H), 4.01–4.16 (m, 2H), 3.71 (s, 3H), 2.30–2.83 (m, 10H), 1.15–1.60 (m, 8H), 0.80–0.95 (m, 3H)

$^{13}$C-NMR (75 MHz, CDCl$_3$) δ213.0, 206.4, 166.8, 147.2, 137.5, 130.4, 121.7, 72.6, 72.0, 54.2, 51.5, 50.4, 45.1, 40.9, 39.8, 37.2, 31.6, 25.9, 25.1, 22.6, 14.0

IR (neat) 3375, 2920, 2860, 1710, 1660, 1440, 1410, 1320, 1280, 1200, 1160, 1070, 1040, 970, 850, 750

$[\alpha]^{22}_D$ −55.1 (c 0.41, CHCl$_3$)

Reference Example 4

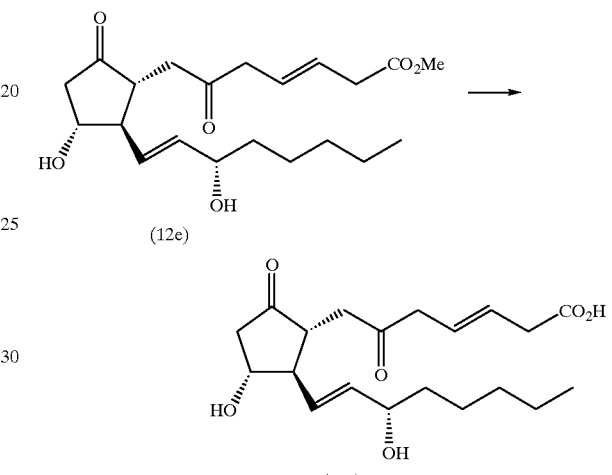

(12e)

(13e)

To 2.5 ml of phosphoric acid buffer at pH 8 was added 0.5 ml of an acetone solution containing 20.4 mg (0.0536 mmol) of a compound (12e). To the solution at room temperature was added 5.3 μl (34 units) of PLE (hog liver esterase, manufactured by Sigma Co.). Stirring was continued at the temperature for 8 hours. After the completion of reaction, the solution was adjusted to pH 4 with 0.1N aqueous hydrochloric acid. Ethyl acetate, 5 ml, was added to the solution, the aqueous layer was saturated with ammonium sulfate, the organic layer was separated, and the aqueous layer was further extracted with 5 ml of ethyl acetate. The organic layer was dried over magnesium sulfate, concentrated, and then purified by silica gel column chromatography, obtaining compound (13e) in an amount of 16.6 mg (0.456 mmol, yield 85%). Analytical data of compound (13e) are shown below.

$^1$H-NMR (300 MHz, CDCl$_3$, (CH$_3$)$_4$Si) δ6.95 (dt, J=15.7, 6.3 Hz, 1H), 5.80 (d, J=15.7 Hz, 1H), 5.45–5.65 (m, 2H), 4.01–4.17 (m, 2H), 2.78 (dd, J=18.4, 7.4 Hz, 1H), 2.31–2.72 (m, 9H), 1.05–1.65 (m, 8H), 0.80–1.00 (m, 3H)

$^{13}$C-NMR (75 MHz, CDCl$_3$) δ213.2, 206.5, 170.0, 149.0, 137.5, 130.4, 121.6, 72.7, 72.1, 53.9, 50.4, 45.2, 40.6, 40.0, 37.0, 31.6, 26.0, 25.2, 22.6, 14.0

IR (neat) 3350, 2910, 2849, 1700, 1650, 1400, 1370, 1280, 1240, 1210, 1160, 1070, 960, 850, 750

$[\alpha]^{22}_D$ −48.1 (c 0.20, MeOH)

Reference Example 5

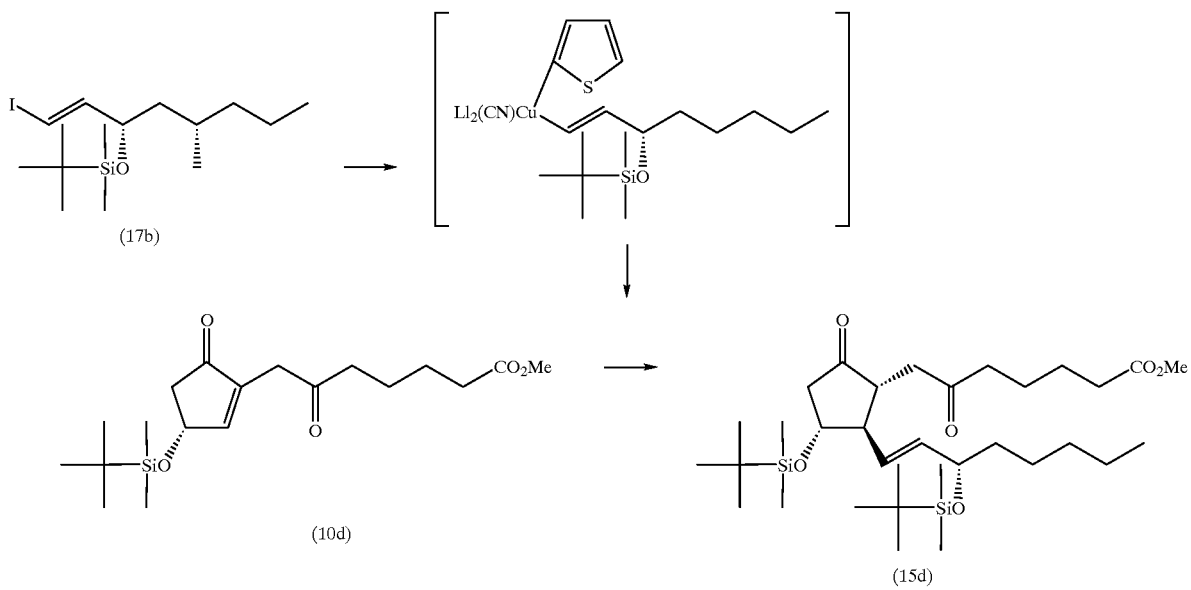

As in Reference Example 1, compound (15d) was obtained by using compounds (10d) and (17b) and carrying out reaction as shown above. Analytical data of compound (15d) are shown below.

$^1$H-NMR (300 MHz, CDCl$_3$, CHCl$_3$) δ5.43–5.56 (m, 2H), 4.02–4.20 (m, 2H), 3.65 (s, 3H), 2.10–2.70 (m, 10H), 0.98–1.70 (m, 13H), 0.86 and 0.87 (2s, 18H), 0.78–0.92 (m, 6H), 0.01 and 0.04 (2s, 12H)

$^{13}$C-NMR (75 MHz, CDCl$_3$) δ214.2, 207.5, 173.7, 136.8, 128.4, 73.4, 71.1, 52.8, 51.5, 49.6, 46.8, 46.2, 42.4, 39.9, 36.8, 33.8, 29.2, 29.1, 25.6, 24.4, 23.1, 18.2, 18.0, 14.1, −4.72, −4.68, −4.57, −4.14 (4C)

IR (neat) 2930, 2850, 1736, 1718, 1460, 1430, 1360, 1240, 1155, 1095, 1050, 1000, 965, 937, 870, 830, 770

$[α]^{21}_D$ −37.5 (c 1.164, CHCl$_3$)

Reference Example 6

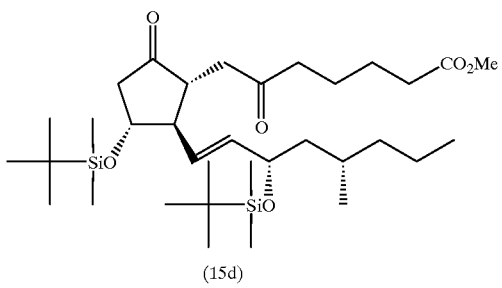

By carrying out reaction as in Reference Example 3, compound (16d) was obtained from compound (15d). Analytical data of compound (16d) are shown below.

$^1$H-NMR (300 MHz, CDCl$_3$, (CH$_3$)$_4$Si) δ5.45–5.60 (m, 2H), 4.00–4.18 (m, 2H), 3.65 (s, 3H), 2.75 (dd, J=18.7, 7.5 Hz, 1H), 2.25–2.69 (m, 9H), 1.05–1.70 (m, 13H), 0.81–1.00 (m, 6H)

$^{13}$C-NMR (75 MHz, CDCl$_3$) δ213.3, 207.8, 173.8, 137.5, 130.8, 72.0, 71.0, 54.2, 51.5, 50.3, 46.9, 45.2, 42.5, 39.7, 36.6, 33.7, 29.5, 29.1, 24.3, 23.1, 22.9, 19.9, 14.1

IR (neat) 3400, 2930, 2850, 1720, 1705, 1435, 1400, 1360, 1245, 1200, 1150, 1070, 970, 830, 720

$[α]^{23}_D$ −35.1 (c 0.70, CHCl$_3$)

EXAMPLE 27

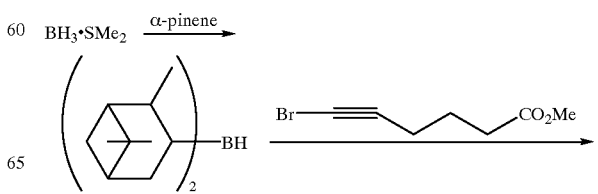

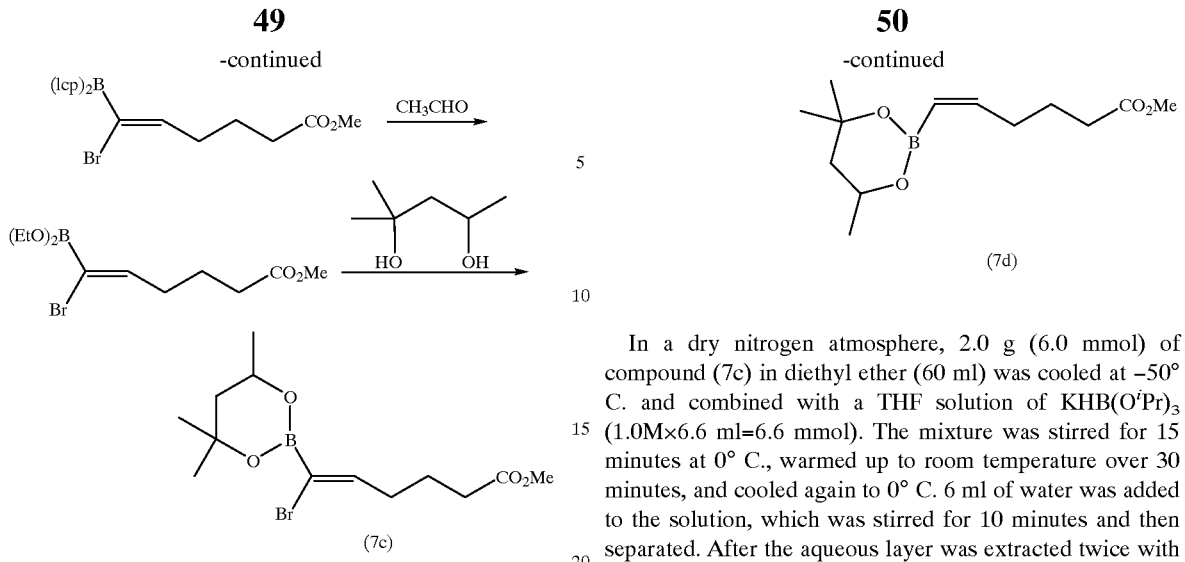

In a dry nitrogen atmosphere, 0.8 ml (8.0 mmol) of borane dimethyl sulfide complex (10.0 M, in THF) was dissolved in 4 ml of dry THF and cooled to 0° C. 2.8 ml (17.6 mmol) of a-pinene was added to the solution, which was stirred for 1 hour at the temperature and warmed up to room temperature over 2 hours. The reaction solution was cooled again at −35° C., combined with 1.7 g (8.3 mmol) of methyl 6-bromo-5-hexynoate in dry THF (4.2 ml), and stirred for 1½ hours at the temperature. The reaction solution was warmed up to room temperature and stirred for 5 hours. The reaction solution was cooled again at 0° C., combined with 7.6 ml (136.3 mmol) of acetaldehyde, and heated under reflux for 12 hours. The solvent, acetaldehyde and isopinocanphenyl residue were distilled off under vacuum at room temperature. A solution of 0.86 ml (6.6 mmol) of 1,3-diol in dry THF (4 ml) was added at room temperature. The mixture was stirred for 3 hours at room temperature and the solvent was distilled off under vacuum. Silica gel short column chromatography yielded 2.3 g of compound (7c) as an oily matter. The yield was 83%. Analytical data of compound (7c) are shown below.

$^1$H-NMR (300 MHz, CDCl$_3$, Me$_4$Si) δ ppm 6.72 (t, J=6.9 Hz, 1H), 4.21–4.32 (m, 1H), 3.67 (s, 3H), 2.28–2.39 (m, 4H), 1.71–1.87 (m, 2H), 1.13–1.38 (m, 11H)

EXAMPLE 28

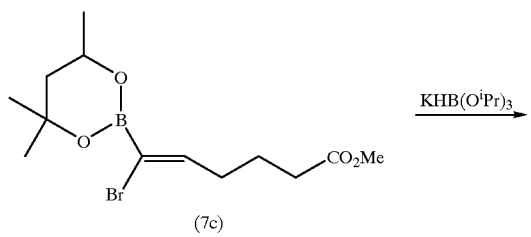

In a dry nitrogen atmosphere, 2.0 g (6.0 mmol) of compound (7c) in diethyl ether (60 ml) was cooled at −50° C. and combined with a THF solution of KHB(O$^i$Pr)$_3$ (1.0M×6.6 ml=6.6 mmol). The mixture was stirred for 15 minutes at 0° C., warmed up to room temperature over 30 minutes, and cooled again to 0° C. 6 ml of water was added to the solution, which was stirred for 10 minutes and then separated. After the aqueous layer was extracted twice with 15 ml of diethyl ether, the organic layer was washed with saturated aqueous sodium chloride solution and dried over anhydrous magnesium sulfate, and the solvent was distilled off under vacuum. Silica gel column chromatography yielded 1.32 g of alkyl borane (7d). The yield was 87%. Analytical data of compound (7d) are shown below.

$^1$H-NMR (300 MHz, CDCl$_3$, Me$_4$Si) δ ppm 6.18–6.30 (m, 1H), 5.27 (d, J=13.7 Hz, 1H), 4.16–4.27 (m, 1H), 3.67 (s, 3H), 2.24–2.49 (m, 4H), 1.13–1.89 (m, 13H)

EXAMPLE 29

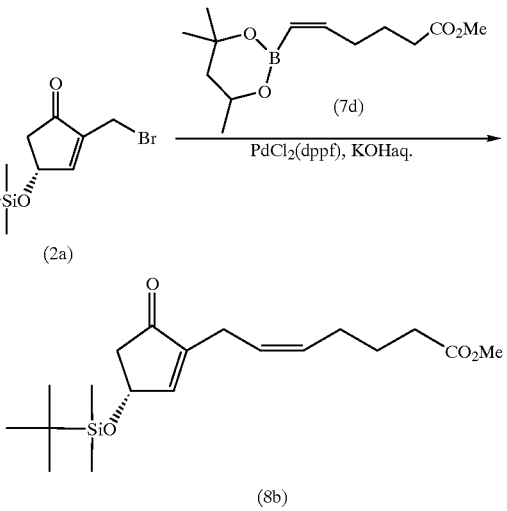

In a dry nitrogen atmosphere, to 140 mg (0.456 mmol) of an enone (2a) in THF (6 ml) at room temperature were added 8 mg (0.012 mmol) of PdCl$_2$(dppf), 232 mg (0.912 mmol) of alkylborane (7d), and 0.22 ml (0.656 mmol) of 3N KOH aqueous solution. The mixture was heated at 60° C. for 30 minutes. The reaction solution was cooled back to room temperature and twice extracted with 5 ml of diethyl ether. The organic layer was washed with 3 ml of 1N HCl aqueous solution, washed with 5 ml of saturated aqueous sodium chloride solution, and dried over anhydrous magnesium sulfate, and the solvent was distilled off under vacuum. Purification by silica gel column chromatography yielded 133 mg of an enone (8b) as an oily matter. The yield was 83%. Analytical data of compound (8b) are shown below.

$^{1}$H-NMR (300 MHz, CDCl$_3$, CHCl$_3$) δ ppm 6.99–7.08 (m, 1H), 5.41–5.53 (m, 2H), 4.83–4.89 (m, 1H), 3.63 (s, 3H), 2.85–2.91(m, 1H), 2.76 (dd, J=18.3, 5.9 Hz, 1H), 2.28 (t, J=7.5 Hz, 2H), 2.26 (dd, J=18.2, 1.9 Hz, 1H), 2.01–2.11 (m, 2H), 1.62–1.72 (m, 2H), 0.88 (s, 9H), 0.09–0.11 (2s, 6H)

$^{13}$C-NMR (75 MHz, CDCl$_3$) δ ppm 205.5, 173.8, 156.8, 145.2, 131.0, 125.5, 68.9, 51.4, 45.4, 33.3, 26.5, 25.7 (3c), 24.6, 22.6, 18.1, −4.73 (2c)

IR (neat) cm$^{-1}$ 2940, 2920, 2870, 2840, 1730, 1700, 1458, 1430, 1350, 1250, 1190

$[α]^{25}_D$ +11.1 (c 1.06, CHCl$_3$)

Reference Example 7

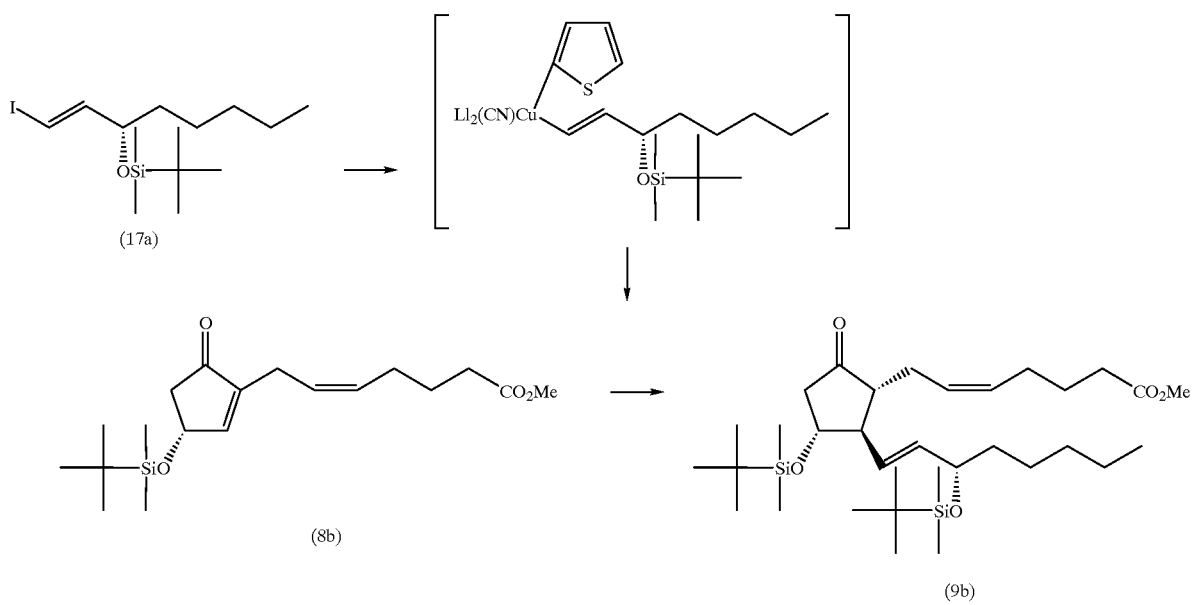

(17a)

(8b)

(9b)

In a nitrogen atmosphere, 0.38 ml (0.652 mmol, concentration in pentane 1.70 M) of t-BuLi was added to 120.1 mg (0.326 mmol) of compound (17a) in diethyl ether (2 ml) at −78° C. and stirred for 30 minutes at the temperature. Next, 1.56 ml (0.391 mmol, concentration in tetrahydrofuran 0.25 M) of lithium 2-thienylcyanocuprate was added thereto, and the mixture was stirred for 20 minutes at −78° C. Moreover, 80.0 mg (0.217 mmol) of an enone (8b) in 1 ml of diethyl ether was added dropwise to the mixture at −78° C. The mixture was warmed up to 0° C. over 2 hours. Reaction was terminated with saturated aqueous ammonium chloride solution and 5 ml of hexane was added for extraction. The aqueous layer was further extracted with 5 ml of hexane. The organic layer was dried over magnesium sulfate, concentrated, and then purified by silica gel column chromatography, obtaining 133 mg of compound (9b) as an oily matter. The yield was 75%. Analytical data of compound (9b) are shown below.

$^{1}$H-NMR (300 MHz, CDCl$_3$, CHCl$_3$) δ ppm 5.59 (dd, J=15.7, 4.0 Hz, 1H), 5.50 (dd, J=15.8, 7.1 Hz, 1H), 5.27–5.45 (m, 2H), 4.01–4.13 (m, 2H), 3.66 (s, 3H), 2.63 (dd, J=18.1, 7.0 Hz, 1H), 2.30 (t, J=7.4 Hz, 2H), 1.99–2.53 (m, 7H), 1.10–1.80 (m, 10H), 0.78–0.96 (m, 3H), 0.88 and 0.89 (2s, 18H), 0.05 and 0.07 (2s, 12H)

$^{13}$C-NMR (75 MHz, CDCl$_3$) δ ppm 215.2, 173.9, 136.4, 130.6, 128.6, 126.7, 73.2, 72.6, 53.9, 52.7, 51.3, 47.7, 38.5, 33.4, 31.8, 26.6, 25.9, 25.8, 25.2, 25.0, 24.7, 22.6, 18.2 (3c), 18.0 (3c), 14.0, −4.32, −4.63, −4.69, −4.75

IR (neat) cm$^{-1}$ 2950, 2925, 2850, 1740, 1460, 1430, 1357, 1250, 1150, 1110, 1090, 1000, 960, 900, 830, 767, 720, $[α]^{25}_D$ +48.6 (c 1.08, CH$_3$OH)

Reference Example 8

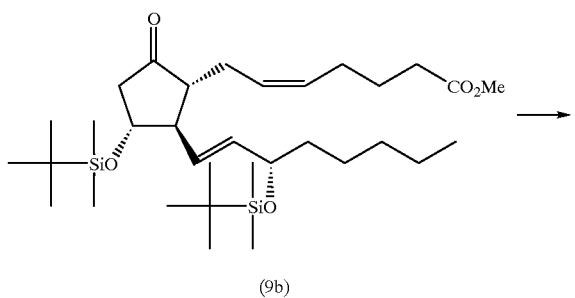

(9b)

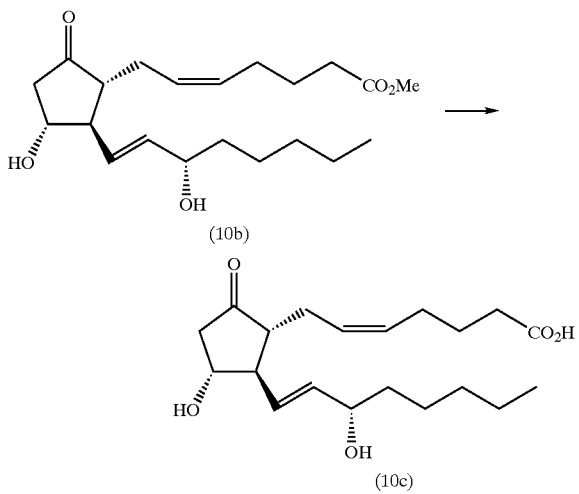

(10b)

In a nitrogen atmosphere, 1.1 ml of pyridine and 0.96 ml of hydrogen fluoride-pyridine complex (containing about 70% of hydrogen fluoride) were added to 336 mg (0.565 mmol) of compound (9b) in 20 ml of acetonitrile at 0° C. The mixture was warmed up to room temperature and stirred for 2 hours at room temperature. The solution was added dropwise to a mixture of 20 ml of saturated aqueous sodium bicarbonate and 20 ml of ethyl acetate. After the organic layer was separated, the aqueous layer was further extracted with 10 ml of ethyl acetate. The organic layers were combined, washed with 8 ml of saturated aqueous sodium bicarbonate, dried over magnesium sulfate, concentrated, and then purified by silica gel column chromatography, obtaining 160 mg of compound (10b) as an oily matter. The yield was 80%. Analytical data of compound (10b) are shown below.

$^1$H-NMR (300 MHz, CDCl$_3$, Me$_4$Si) δ ppm 5.67 (dd, J=15.3, 6.5 Hz, 1H), 5.57 (dd, J=15.2, 7.6 Hz, 1H), 5.28–5.45 (m, 2H), 4.04–4.15 (m, 2H), 3.66 (s, 3H), 2.75 (dd, J=18.5, 7.2 Hz, 1H), 2.30 (t, J=7.4 Hz, 2H), 2.00–2.43 (m, 7H), 1.25–1.71 (m, 10H), 0.89 (t, J=6.8 Hz, 3H)

Reference Example 9

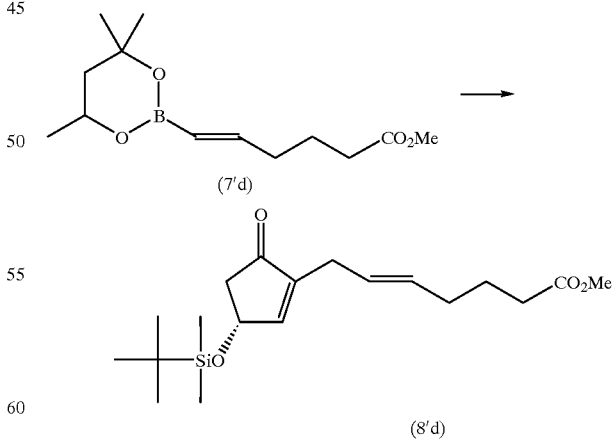

To 152 mg (0.415 mmol) of PGE$_2$ methyl ester (10b) were added 18 ml of phosphoric acid buffer (KH$_2$PO$_4$—Na$_2$HPO$_4$, 1 M, pH 8.0) and 8 ml of acetone. To this solution, 0.21 ml of Polcine Liver Esterase (785 units, in aqueous (NH$_4$)$_2$SO$_4$ solution) was added at room temperature, followed by rigorous stirring at room temperature for 6 hours. The solution was adjusted to pH 4 with an aqueous solution of 1N HCl, and (NH$_4$)$_2$SO$_4$ was added until it was saturated. The solution was extracted twice with 25 ml of ethyl acetate. The organic layers were combined, washed with 5 ml of saturated aqueous sodium chloride solution, dried over magnesium sulfate, concentrated, and purified by silica gel column chromatography, obtaining 146 mg of compound (10c) as an oily matter. The yield was 91%. Analytical data of compound (10c) are shown below.

$^1$H-NMR (300 MHz, CDCl$_3$, Me$_4$Si) δ ppm 5.67 (dd, J=15.3, 6.5 Hz, 1H), 5.57 (dd, J=15.2, 7.6 Hz, 1H), 5.31–5.46 (m, 2H), 4.00–4.17 (m, 2H), 2.75 (dd, J=18.5, 7.2 Hz, 1H), 2.33 (t, J=6.8 Hz, 2H), 1.95–2.43 (m, 7H), 1.25–1.73 (m, 10H), 0.89 (t, J=6.7 Hz, 3H)

$^{13}$C-NMR (75 MHz, CDCl$_3$) δ ppm 214.6, 177.2, 136.6, 131.2, 130.8, 126.7, 73.1, 72.0, 54.4, 53.4, 46.2, 36.9, 33.1, 31.6, 26.4, 25.2, 25.1, 24.5, 22.6, 14.0

This compound is a naturally occurring one and known in the literature. The overall synthesis of PGE$_2$ was thus successful.

Reference Example 10

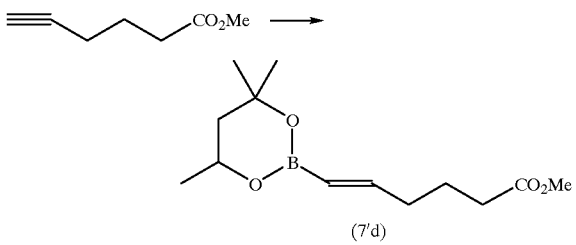

By following the same process as compound (7c), trans compound (7'd) was obtained in a yield of 72% from methyl 5-hexynoate. Analytical data of compound (7'd) are shown below.

$^1$H-NMR (300 MHz, CDCl$_3$, Me$_4$Si) δ ppm 6.47 (dt, J=17.6, 6.4 Hz, 1H), 5.36 (dt, J=17.7, 1.5 Hz, 1H); 4.10–4.27 (m, 1H), 3.65 (S, 3H), 2.15–2.40 (m, 4H), 1.15–1.82 (m, 13H)

Reference Example 11

By following the same process as compound (8b), trans compound (8'b) was obtained in a yield of 72% from compound (7'd). Analytical data of compound (8'b) are shown below.

$^1$H-NMR (300 MHz, CDCl$_3$, CHCl$_3$) δ ppm 7.01–7.04 (m, 1H), 5.43–5.49 (m, 2H), 4.85–4.90 (m, 1H), 3.65 (S, 3H), 2.83–2.88 (m, 2H), 2.74 (dd, J=18.3, 5.9 Hz, 1H), 2.30 (t, J=7.5 Hz, 2H), 2.27 (dd, J=18.3, 2.1 Hz, 1H), 2.00–2.09 (m, 2H), 1.62–1.75 (m, 2H), 0.90 (s, 9H), 0.01 and 0.11 (2s, 11H)

$^{13}$C-NMR (75 MHz, CDCl$_3$) δ ppm 205.5, 174.0, 157.1, 145.9, 132.0, 126.2, 69.0, 51.4, 45.5, 33.3, 31.7, 27.7, 25.8, 24.4, 18.1, −4.70 (2c)

IR (neat) cm$^{-1}$ 2960, 2940, 2865, 1740, 1720, 1640, 1470, 1440, 1370, 1300, 1260, 1200, 1170, 1080, 1010, 970, 903, 840, 820, 780, 670

$[α]^{24}_D$ +10.5 (c 0.97, CHCl$_3$)

EXAMPLE 32

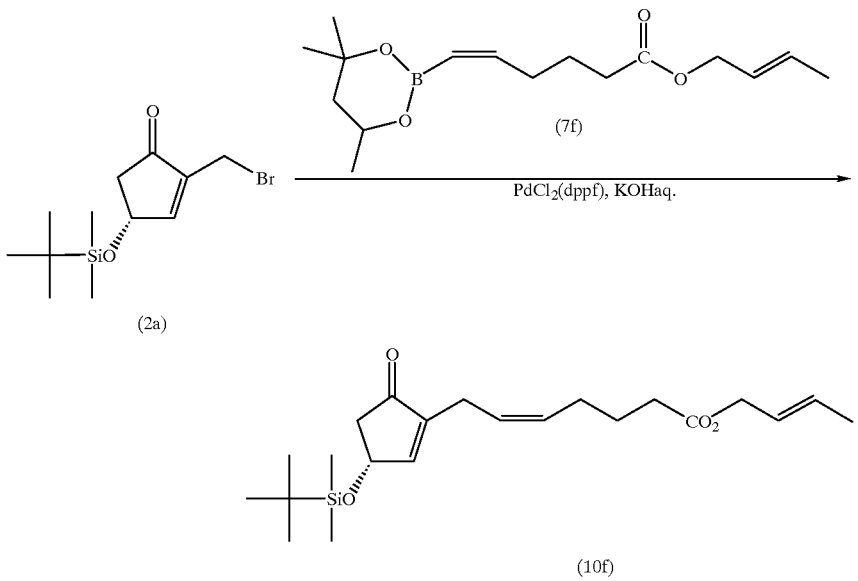

In a dry nitrogen atmosphere, 6.3 mg (0.0086 mmol) of PdCl$_2$(dppf), 201 mg (0.684 mmol) of alkylborane (7f) and 0.33 ml (1.026 mmol) of an aqueous 3N KOH solution were added to 105 mg (0.342 mmol) of an enone (2a) in 3.6 ml of THF at room temperature and heated at 50° C. for 1 hour. The reaction solution was cooled back to room temperature, and extracted twice with 5 ml of diethyl ether. The organic layer was washed with 3 ml of an aqueous solution of 1N HCl and then with 5 ml of saturated aqueous sodium chloride solution and dried over anhydrous magnesium sulfate, and the solvent was distilled off in vacuum. Silica gel column chromatography gave 109 mg of compound (10f). The yield was 81%. Analytical data of compound (10f) are shown below.

$^1$H-NMR (300 MHz, CDCl$_3$, CHCl$_3$) δ ppm 5.72–5.82 (m, 1H), 5.43–5.63 (m, 3H), 4.86–4.91 (m, 1H), 4.49 (d, J=6.4 Hz), and 4.63 (d, J=6.8 Hz, 2H), 2.75 (dd, J=18.3, 5.9 Hz, 1H), 2.31 (t, J=7.6 Hz, 2H), 2.28 (dd, J=18.3, 2.0 Hz, 1H), 2.05–2.13 (m, 2H), 1.64–1.76 (m, 5H), 0.90 (S, 9H), 0.11 and 0.12 (2s, 6H)

$^{13}$C-NMR (75 MHz, CDCl$_3$) δ ppm 205.5, 173.2, 156.8, 145.7, 131.2, 131.1, 129.4, 129.3, 125.5, 125.2, 69.0, 59.9, 45.5, 33.6, 26.5, 25.8 (3c), 24.6, 22.6, 18.1, 17.7, −4.71 (2c)

IR (neat) cm$^{-1}$ 2970, 2950, 2870, 1740, 1720, 1475, 1395, 1360, 1265, 1200, 1170, 1095, 1050, 1020, 980, 910, 845, 820, 785

$[α]^{25}_D$ +11.3 (c 0.96, CDCl$_3$)

Reference Example 12

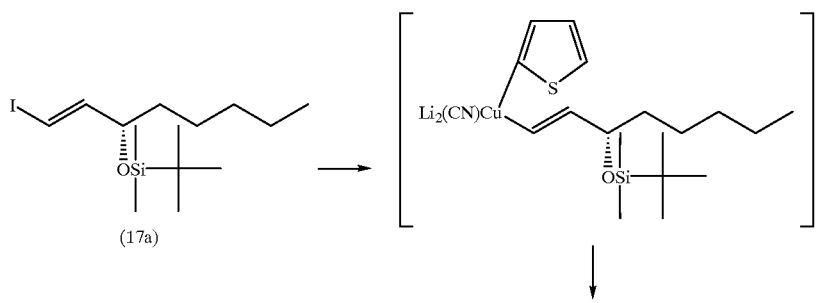

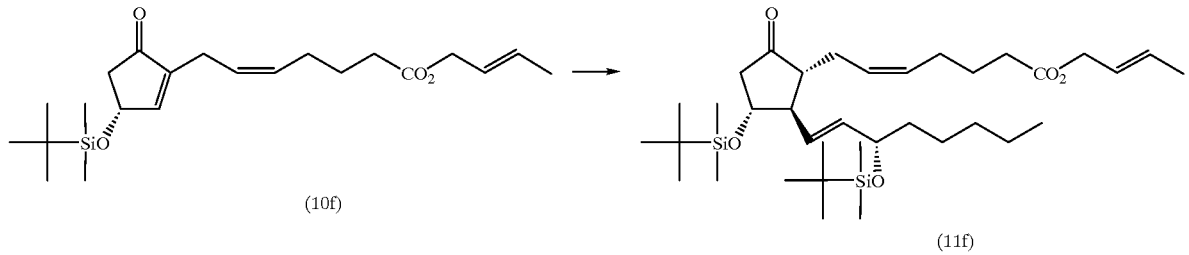

(10f) → (11f)

In a dry nitrogen atmosphere, 0.9 ml (1.528 mmol, concentration in pentane 1.70 M) of t-BuLi was added to 281 mg (0.764 mmol) of compound (17a) in 3.82 ml of diethyl ether at −78° C., and the mixture was stirred for 30 minutes at the temperature. Next, 3.66 ml (0.916 mmol, concentration in tetrahydrofuran 0.25 M) of lithium 2-thienylcyanocuprate was added thereto, and the mixture was stirred for 30 minutes at −78° C. Moreover, 1 ml of a diethyl ether solution containing 107 mg (0.273 mmol) of an enone (10f) was added dropwise to the mixture at −78° C. The mixture was warmed up to 0° C. over 2 hours. Reaction was terminated with 5 ml of saturated aqueous ammonium chloride solution, and 5 ml of diethyl ether was added for extraction. The aqueous layer was further extracted with 5 ml of diethyl ether. The organic layer was dried over magnesium sulfate, concentrated, and then purified by silica gel column chromatography, obtaining 151 mg of compound (11f) as an oily matter. The yield was 87%. Analytical data of compound (11f) are shown below.

$^1$H-NMR (300 MHz, CDCl$_3$, CHCl$_3$) δ ppm 5.71–5.82 (m, 1H), 5.29–5.63 (m, 3H), 4.49 (d, J=6.5 Hz) and 4.63 (d, J=6.8 Hz, 2H), 4.01–4.13 (m, 2H), 2.63 (dd, J=18.4, 7.1 Hz, 1H), 2.29 (t, J=7.7 Hz, 2H), 1.97–2.53 (m, 7H), 1.13–1.80 (m, 13H), 0.81–0.98 (m, 3H), 0.87 and 0.89 (2s, 18H), 0.04 and 0.05 (2s, 12H)

Reference Example 13

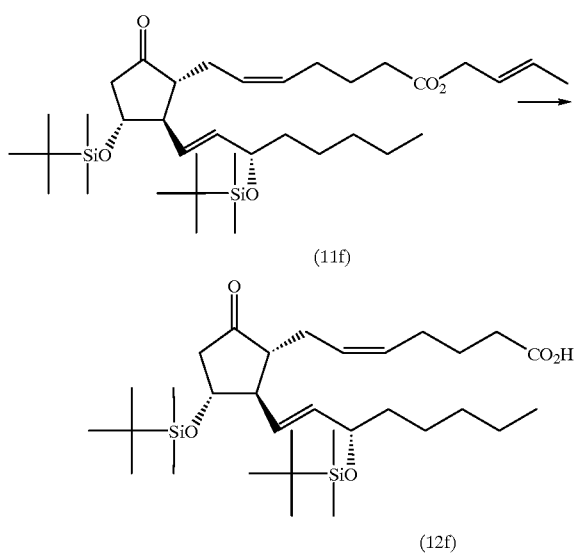

(11f)

(12f)

In a dry argon atmosphere, 0.022 ml (0.579 mmol) of formic acid, 0.07 ml (0.492 mmol) of triethylamine, and 0.0163 ml (0.0656 mmol) of tributylphosphine were added to 17 mg (0.0164 mmol) of Pd$_2$(dba)$_3$·CHCl$_3$ in 2.2 ml of dry THF at room temperature, which was stirred for 30 minutes. A solution of 100 mg (0.16 mmol) of compound (11f) in 1 ml of THF was added thereto and stirred for 40 minutes at 40° C. Reaction was terminated with 5 ml of aqueous 1N hydrochloric acid. After the aqueous layer was twice extracted with diethyl ether, the organic layer was washed with saturated aqueous sodium chloride solution and dried over anhydrous magnesium sulfate, and the solvent was distilled off under vacuum. Silica gel column chromatography gave 75 mg of compound (12f). The yield was 82%. Analytical data of compound (12f) are shown below.

$^1$H-NMR (300 MHz, CDCl$_3$, Me$_4$Si) δ ppm 5.59 (dd, J=15.3, 4.8 Hz, 1H), 5.50 (dd, J=15.4, 7.3 Hz, 1H), 5.30–5.45 (m, 2H), 4.01–4.14 (m, 2H), 2.63 (dd, J=18.3, 6.7 Hz, 1H), 2.34 (t, J=7.5 Hz, 2H), 1.99–2.53 (m, 7H), 1.62–1.78 (m, 2H), 1.16–1.57 (m, 8H), 0.81–1.00 (m, 3H), 0.87 and 0.89 (2s, 18H), 0.04 and 0.05 (2s, 12H)

Reference Example 14

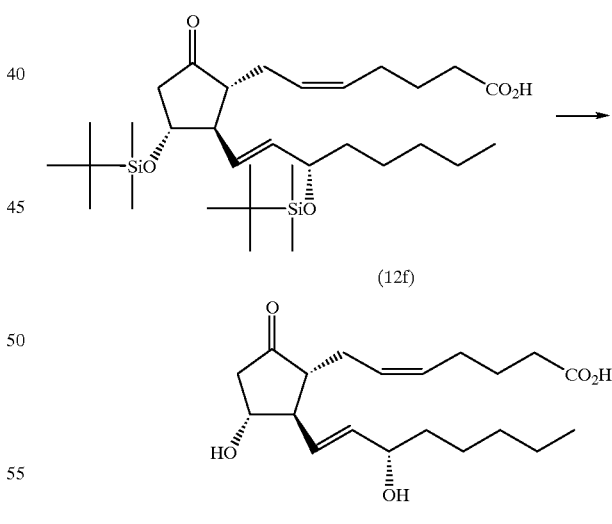

(12f)

(13f)

In a dry nitrogen atmosphere, 0.4 ml of pyridine was added to 110 mg (0.189 mmol) of compound (12f) in 6.8 ml of acetonitrile, which was cooled to 0° C. 0.32 ml of hydrogen fluoride pyridine complex was added thereto, and the mixture was warmed up to room temperature and stirred for 4 hours at room temperature. Reaction was terminated with 5 ml of saturated aqueous sodium bicarbonate, 5 ml of ethyl acetate was added, $(NH_4)_2SO_4$ was added until it was saturated, and extraction was done. The aqueous layer was further extracted with 5 ml of ethyl acetate. The organic layer was dried over magnesium sulfate, concentrated, filtered through a silica gel pad, and then concentrated. It was purified by silica gel column chromatography, obtaining 61 mg of compound (13f). The yield was 92%. Analytical data of compound (13f) was identical with compound (10c).

What is claimed is:

1. A method for preparing a substituted cyclopentene derivative of the formula (IX):

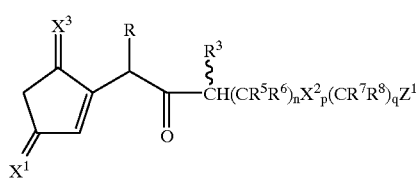

(IX)

wherein R, $X^1$, $X^3$, $R^3$, $R^5$, $R^6$, $R^7$, $R^8$, $X^2$, n, p, q, and $Z^1$ are as defined below, said method comprising the step of subjecting to acidolysis a substituted cyclopentene derivative of the formula (VIII):

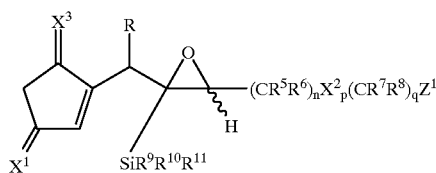

(VIII)

wherein R is a hydrogen atom, alkyl radical having 1 to 6 carbon atoms, alkenyl radical having 2 to 6 carbon atoms, allynyl radical having 2 to 6 carbon atoms, cycloalkyl radical having 3 to 8 carbon atoms, aralkyl radical having 7 to 19 carbon atoms, aryl radical having 6 to 12 carbon atoms, alkoxy radical having 1 to 6 carbon atoms, alkenyloxy radical having 2 to 6 carbon atoms, alkylthio radical having 1 to 6 carbon atoms, or alkenylthio radical having 2 to 6 carbon atoms;

$R^3$ is a hydrogen atom, alkyl radical having 1 to 6 carbon atoms, alkenyl radical having 2 to 6 carbon atoms, alkenyl radical having 2 to 6 carbon atoms, or cyclohexyl radical having 3 to 8 carbon atoms;

$R^5$, $R^6$, $R^7$, and $R^8$ are independently selected from the group consisting of a hydrogen atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxycarbonyl radical, and alkenyloxycarbonyl radical;

$R^9$, $R^{10}$ and $R^{11}$ are independently selected from the group consisting of a hydrogen atom, chlorine atom, fluorine atom, alkyl radical having 1 to 6 carbon atoms, alkenyl radical having 2 to 6 carbon atoms, alkynyl radical having 2 to 6 carbon atoms, cycloalkyl radical having 3 to 8 carbon atoms, alkoxy radical having 1 to 6 carbon atoms, alkenyloxy radical having 2 to 6 carbon atoms, phenyl radical, tolyl radical, and benzyl radical;

$X^1$ is ($\alpha$-$OZ^a$, $\beta$-H) or ($\alpha$-H, $\beta$-$OZ^a$), $X^3$ is ($\alpha$-$OZ^d$, $\beta$-H), ($\alpha$-H, $\beta$-$OZ^d$) or an oxygen atom, each of $Z^a$ and $Z^d$, which may be the same or different, is a hydrogen atom or a protective radical for a hydroxyl radical;

$X^2$ is a $CR^{12}$=$CR^{13}$ radical, C≡C, phenylene radical, carbonyl radical, oxygen atom, or sulfur atom, wherein $R^{12}$ and $R^{13}$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms;

p is an integer of 0 or 1, each of n and q is an integer of 0 to 5; and $Z^1$ is a hydrogen atom, $COOR^y$, CN, OH, $OCOR^z$, $CONR^bR^c$, or $NR^dR^e$ wherein $R^y$ and $R^z$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^b$ and $R^c$ are independently selected from the group consisting of a hydrogen atom, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms, $R^d$ and $R^e$ are independently selected from the group consisting of a hydrogen atom, benzyl radical, phenyl radical, alkyl radical having 1 to 6 carbon atoms, alkenyl radical having 2 to 6 carbon atoms, alkynyl radical having 2 to 6 carbon atoms, and cycloalkyl radical having 3 to 8 carbon atoms.

2. The method of claim 1, wherein said acidolysis is effected by a Lewis acid, a mineral acid, or an organic acid.

3. The method of claim 2, wherein said acidolysis is effected by a boron trifluoride diethyl ether complex.

* * * * *